(12) United States Patent
Ametamey et al.

(10) Patent No.: US 8,344,140 B2
(45) Date of Patent: Jan. 1, 2013

(54) $^{18}$F-LABELLED FOLATES

(75) Inventors: Simon Mensah Ametamey, Zurich (CH); Rudolf Moser, Schaffhausen (CH); Tobias Ludwig Ross, Zurich (CH); Thomas Leighton Mindt, Basel (CH); Viola Groehn, Dachsen (CH)

(73) Assignee: Merck Eprova AG, Schaffhausen (CH)

( * ) Notice: Subject to any disclaimer, the term of this patent is extended or adjusted under 35 U.S.C. 154(b) by 163 days.

(21) Appl. No.: 12/595,297

(22) PCT Filed: Apr. 11, 2008

(86) PCT No.: PCT/EP2008/054406
§ 371 (c)(1),
(2), (4) Date: Oct. 9, 2009

(87) PCT Pub. No.: WO2008/125615
PCT Pub. Date: Oct. 23, 2008

(65) Prior Publication Data
US 2010/0111863 A1 May 6, 2010

(30) Foreign Application Priority Data

Apr. 11, 2007 (EP) .................................. 07105984

(51) Int. Cl.
*A61K 31/41* (2006.01)
*C07D 249/00* (2006.01)
*C07D 257/04* (2006.01)

(52) U.S. Cl. ........................................ 544/259; 548/255
(58) Field of Classification Search ................. 544/259; 548/255
See application file for complete search history.

(56) References Cited

U.S. PATENT DOCUMENTS

| | | | |
|---|---|---|---|
| 4,115,065 A | 9/1978 | Bayly et al. | |
| 4,202,976 A | 5/1980 | Bayly et al. | |
| 4,276,280 A | 6/1981 | Akerkar et al. | |
| 4,298,735 A | 11/1981 | Farina et al. | |
| 4,314,988 A | 2/1982 | Farina et al. | |
| 4,326,060 A | 4/1982 | Farina et al. | |
| 4,337,339 A | 6/1982 | Farina et al. | |
| 4,584,375 A | 4/1986 | Coward | |
| 4,628,090 A | 12/1986 | Coward | |
| 5,066,828 A | 11/1991 | Bey et al. | |
| 5,286,726 A | 2/1994 | Bey et al. | |
| 2005/0227985 A9 * | 10/2005 | Green et al. ................. | 514/243 |

FOREIGN PATENT DOCUMENTS

| | | |
|---|---|---|
| EP | 0451835 A1 | 10/1991 |
| EP | 0451836 A2 | 10/1991 |
| GB | 1501119 A | 2/1978 |
| JP | 61044890 A | 3/1986 |
| JP | 61044890 W | 3/1986 |
| WO | 2006071754 A2 | 7/2006 |
| WO | WO 2006/171754 A * | 7/2006 |
| WO | 2006116629 A2 | 11/2006 |
| WO | 2008098112 A2 | 8/2008 |
| WO | PCTEP2008054406 | 8/2008 |

OTHER PUBLICATIONS

Bettio et al, J. Nuclear Medicine, vol. 47, 2005, pp. 1153-1160, esp. p. 1156.*
Marik, et al., Tet. Lett., vol. 47(No. 37), 2006, pp. 6681-6684.*
Betrio, A. et al., "Synthesis and Preclinical Evaluation of a Folic Acid Derivative Labeled with 18F for PET Imaging of Folate Receptor-Positive Tumors." (Journal of Nuclear Medicine), 2006, 1153-1160, vol. 47.
Marik, J. et al., "Click for PET: Rapid Preparation of [18F]-fluoropeptides using Cu(I) Catalysed 1,3-Dipolar Cycloaddition." (Tetrahedron Letters), 2006, 6681-6684, vol. 47.
Ross, T.L. et al., "Radiosynthesis of 18F-labelled folic acid derivatives using a direct method and "click chemistry"." (Journal of Labelled Compounds and Radiopharmaceuticals), Apr. 11, 2007, S35, vol. 50.

* cited by examiner

*Primary Examiner* — Susannah Chung
(74) *Attorney, Agent, or Firm* — Millen, White, Zelano & Branigan, P.C.

(57) ABSTRACT

The present invention is directed towards new $^{18}$F-folate radiopharmaceuticals, wherein fluorine-18 is covalently linked through a triazole- or tetrazole linker to a folate or derivative thereof, a method of their preparation, as well as their use in diagnosis and monitoring of therapy of cancer and inflammatory and autoimmune diseases.

23 Claims, 4 Drawing Sheets

18F-LABELLED FOLATES

FIELD OF INVENTION

The present invention is directed towards new $^{18}$F-folate radiopharmaceuticals, wherein fluorine-18 is covalently linked through a triazole- or tetrazole-linker to a folate or derivative thereof, a method of their preparation, as well as their use in diagnosis and monitoring of cancer and inflammatory and autoimmune diseases and therapy thereof.

BACKGROUND

Cell-specific targeting for delivery of effector moieties such as diagnostic or therapeutic agents is a widely researched field and has led to the development of non-invasive diagnostic and/or therapeutic medical applications. In particular in the field of nuclear medicine procedures and treatments, which employ radioactive materials emitting electromagnetic radiations as γ-rays or photons or particle emitting radiation, selective localization of these radioactive materials in targeted cells or tissues is required to achieve either high signal intensity for visualization of specific tissues, assessing a disease and/or monitoring effects of therapeutic treatments, or high radiation dose, for delivering adequate doses of ionizing radiation to a specified diseased site, without the risk of radiation injury in other e.g. healthy tissues. It is thus of crucial interest to determine and assess cell-specific structures and in particular structures that are present in case of tumors (i.e. cancer) or inflammatory and autoimmune diseases, such as receptors, antigens, haptens and the like which can be specifically targeted by the respective biological vehicles.

The folate receptor (FR) has been identified as one of these structures. The FR is a high-affinity ($K_D < 10^{-9}$ M) membrane-associated protein. In normal tissues and organs FR-expression is highly restricted to only a few organs (e.g. kidney, lungs, choroids plexus, and placenta), where it largely occurs at the luminal surface of epithelial cells and is therefore not supplied with folate in the circulation. The FR-alpha is frequently overexpressed on a wide variety of specific cell types, such as epithelial tumours (e.g. ovarian, cervical, endometrial, breast, colorectal, kidney, lung, nasopharyngeal), whereas the FR-beta is frequently overexpressed in leukaemia cells (approx. 70% of acute myelogenous leukaemia (AML) are FR-beta positive). Both may therefore be used as a valuable tumour marker for selective tumour-targeting (Elnakat and Ratnam, Adv. Drug Deliv. Rev. 2004; 56:1067-84). In addition it has recently been discovered that activated (but not resting) synovial macrophages in patients diagnosed with rheumatoid arthritis possess a functionally active FR-beta (Nakashima-Matsushita et al, Arthritis & Rheumatism, 1999, 42(8): 1609-16). Therefore activated macrophages can be selectively targeted with folate conjugates in arthritic joints, a capability that opens possibilities for the diagnosis and treatment of rheumatoid arthritis (Paulos et al, Adv. Drug Deliv. Rev. 2004; 56:1205-17).

Folic acid, which is based on a pteridine skeleton which is conjugated through a benzoylamino moiety to a glutamate, and its derivatives have thus been intensively studied over the past 15 years as targeting agents for the delivery of therapeutic and/or diagnostic agents to cell populations bearing folate receptors in order to achieve a selective concentration of therapeutic and/or diagnostic agents in such cells relative to normal cells. Various folic acid derivatives and conjugates are known and have been (pre)clinically evaluated, including folate radiopharmaceuticals (Leamon and Low, Drug Discov. Today 2001; 6:44-51; U.S. Pat. No. 4,276,280), fluorinated folate chemotherapeutics (U.S. Pat. No. 4,628,090), folate-conjugates with chemotherapeutic agents (Leamon and Reddy, Adv. Drug Deliv. Rev. 2004; 56:1127-41; Leamon et al, Bioconjugate Chem. 2005; 16:803-11), with proteins and protein toxins (Ward et al., J. Drug Target. 2000; 8:119-23; Leamon et al, J. Biol. Chem. 1993; 268:24847-54; Leamon and Low, J. Drug Target. 1994; 2:101-12), with antisense oligonucleotides (Li et al, Pharm. Res. 1998; 15:1540-45; Zhao and Lee, Adv. Drug Deliv. Rev. 2004; 56:1193-204), with liposomes (Lee and Low, Biochim. Biophys. Acta-Biomembr. 1995; 1233:134-44; Gabizon et al, Adv. Drug Deliv. Rev. 2004; 56:1177-92), with hapten molecules (Paulos et al, Adv. Drug Deliv. Rev. 2004; 56:1205-17), with MRI contrast agents (Konda et al, Magn. Reson. Mat. Phys. Biol. Med. 2001; 12:104-13) etc. Typically all of these derivatives and conjugates have been modified at the glutamate portion of folic acid which lends itself to known carboxylic acid coupling methodology.

Folate radiopharmaceuticals can be in particular very useful for an improved diagnosis and evaluation of the effectiveness of cancer and inflammatory and autoimmune disease therapy. This may include assessment and/or prediction of a treatment response and consequently improvement of radiation dosimetry. Typical visualization techniques suitable for radioimaging are known in the art and include positron emission tomography (PET), planar or single photon emission computerized tomography (SPECT) imaging, gamma cameras, scintillation, and the like.

Both PET and SPECT use radiotracers to image, map and measure activities of target sites of choice. Yet while PET uses positron emitting nuclides which require a nearby cyclotron, SPECT uses single photon emitting nuclides which are available by generator systems, which may make its use more convenient. However SPECT provides less sensitivity than PET and beside a few approaches quantification methods are lacking. In case of PET, the positron annihilation results in two gamma rays of 511 keV which provide the basis for well developed quantification methods. Thus PET is one of the most sophisticated functional imaging technologies to assess regional uptake and affinity of ligands or metabolic substrates in brain and other organs and thus provides measures of imaging based on metabolic activity. This is for example achieved by administering a positron emitting isotope to a subject, and as it undergoes radioactive decay the gamma rays resulting from the positron/electron annihilation are detected by the PET scanner.

Factors that need to be considered in the selection of a suitable isotope useful for PET include sufficient half-life of the positron-emitting isotope to permit preparation of a diagnostic composition optionally in a pharmaceutically acceptable carrier prior to administration to the patent, and sufficient remaining half-life to yield sufficient activity to permit extracorporeal measurement by a PET scan. Furthermore, a suitable isotope should have a sufficiently short half-life to limit patient exposure to unnecessary radiation. Typically, a suitable radiopharmaceutical for PET may be based on a metal isotope, such as gallium or copper. These two require however a chelator for entrapment of the metal, which may have an effect on steric and chemical properties. Alternatively a radiopharmaceutical may be based on a covalently linked isotope which provides minimal structural alteration. Radionuclides used for covalent attachment and suitable for PET scanning are typically isotopes with short half lives such as $^{11}$C (ca. 20 min), $^{13}$N (ca. 10 min), $^{15}$O (ca. 2 min), $^{18}$F (ca. 110 min).

To date, a number of chelate-based folate radiopharmaceuticals have been synthesized and successfully evaluated as diagnostic agents for imaging folate receptor-positive tumors. The most widely studied derivatives were labeled either with $^{111}$In and $^{99m}$Tc (Siegel et al., J. Nucl. Med. 2003, 44:700; Müller et al., J. Organomet. Chem. 2004, 689:4712) for SPECT or with $^{68}$Ga for PET (Mathias et al., Nucl. Med. Biol. 2003, 30(7):725). However, all of the above need a suitable chelating agent, which is typically linked to folic acid through its glutamate portion.

Thus a folate radiopharmaceutical having a covalently linked isotope would be of great interest. In particular a $^{18}$F-labeled folate radiopharmaceutical would be most suitable for PET Imaging because of its excellent imaging characteristics which would fulfil all of the above considerations. Compared with other suitable radionuclides ($^{11}$C, $^{13}$N, $^{15}$O), $^{18}$F is very useful because of its long half-life of approximately 110 minutes and because it decays by emitting positrons having the lowest positron energy, which allows for the sharpest images with a high-resolution PET. Furthermore, the longer half-life of $^{18}$F also allows for syntheses that are more complex and satellite distribution to PET centers with no radiochemistry facilities.

Yet, the structure of folic acid does not lend itself to direct radiolabeling with $^{18}$F. Thus to date, there have been only very few $^{18}$F-labeled folic acid derivatives reported in the literature (Bettio et al., J. Nucl. Med., 2006, 47(7), 1153; WO 2006/071754). Moreover, the currently reported radiosyntheses are time-consuming and give only low radiochemical yields of less than 5% (Bettio et al., J. Nucl. Med., 2006, 47(7), 1153). Thus currently known $^{18}$F-labeled folates or derivatives thereof are not able to fill the need for specific radiopharmaceuticals suitable for metabolic imaging of tumors to improve diagnosis and treatment of cancer and inflammatory and autoimmune diseases.

Applicants have now found efficient and versatile methods for production of new $^{18}$F-labeled folate radiopharmaceuticals wherein fluorine-18 is linked through a triazole or tetrazole-linker to a folate or derivative thereof, such as e.g. to the glutamate functionality of folic acid. Preliminary in-vitro studies suggested their suitability as powerful diagnostic agents for FR-positive tumours.

SUMMARY OF THE INVENTION

The present invention is in a first aspect directed to new $^{18}$F-folate radiopharmaceuticals (hereinafter also called compounds of the invention), wherein fluorine-18 is linked through a triazole or tetrazole linker to a folate or derivative thereof, such as to the glutamate functionality of folate or derivative.

In one specific embodiment, the new folate radiopharmaceuticals are compounds of formula I,

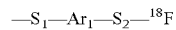

P—S$_1$—Ar$_1$—S$_2$—$^{18}$F     I wherein
P is a folate or derivative thereof,
S$_1$, S$_2$ are independently of each other a single bond or a spacer, and
Ar$_1$ is a triazole or tetrazole.

Preferably S$_1$ and S$_2$ are independently of each other a single bond or a spacer unit, such as straight chain or branched C$_1$-C$_{12}$ alkyl, which is unsubstituted or substituted by at least one —CN, -Hal, —OH, —NH$_2$, —SH, —SO$_3$H or —NO$_2$, and wherein one or more of the non-adjacent CH$_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —SO$_3$R'—, —PR'— or a five- or six-membered aromatic ring, which is unsubstituted or substituted with —CN, -Hal, —NO$_2$, —COR' or —COOR', wherein R' represents H or C$_1$-C$_6$ alkyl, or a combination thereof.

More specifically the present invention is directed towards compounds having formula II

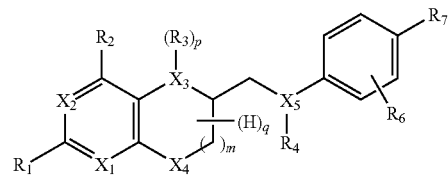

wherein
X$_1$ to X$_5$ are independently of each other C or N
R$_1$ and R$_2$ are independently of each other H, Hal, —OR', —NHR', C1-C12 alkyl, C$_1$-C$_{12}$ alkoxy, C$_1$-C$_{12}$ alkanoyl, C$_2$-C$_{12}$ alkenyl, C$_2$-C$_{12}$ alkynyl, (C$_1$-C$_{12}$ alkoxy)carbonyl, and (C$_1$-C$_{12}$ alkylamino)carbonyl, wherein R' is H or C1-C6 alkyl,
R$_3$, R$_4$ are independently of each other H, formyl, iminomethyl, nitroso, C1-C12 alkyl, C1-C12 alkoxy, C1-C12 alkanoyl, halosubstituted C1-C12 alkanoyl,
R$_5$ is H, C$_1$-C$_{12}$ alkyl, C$_1$-C$_{12}$ alkoxy, C$_1$-C$_{12}$ alkanoyl, C$_2$-C$_{12}$ alkenyl, C$_2$-C$_{12}$ alkynyl, (C$_1$-C$_{12}$ alkoxy)carbonyl, and (C$_1$-C$_{12}$ alkylamino) carbonyl,
R$_6$, R$_7$ are independently of each other straight-chain or branched C$_1$-C$_{12}$ alkyl, which is unsubstituted or substituted by at least one CN, Hal, or NO$_2$, or a group of the formula III —S$_1$—Ar$_1$—S$_2$—$^{18}$F     III wherein S$_1$ and S$_2$ are independently of each other a single bond or a spacer unit, such as straight-chain or branched C$_1$-C$_{12}$ alkyl, which is unsubstituted or substituted by at least one CN, Hal, or NO$_2$, and wherein one or more of the non-adjacent CH$_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —SO$_3$R'—, —PR'— or a five- or six-membered aromatic ring, which is unsubstituted or substituted with CN, Hal, NO$_2$, COR', or COOR', wherein R' represents H or C$_1$-C$_6$ alkyl, or a combination thereof, and
Ar$_1$ is a triazole or a tetrazole,
with the proviso that one of R$_6$ and R$_7$ is a group of formula III,
m is 0 or 1,
P is 0, 1 or 2, and
q has a value of 1 to 7.

In a further specific embodiment the present invention contemplates a compound of formula IV

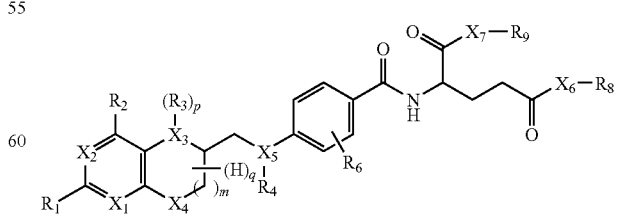

wherein
X$_6$, X$_7$ are independently of each other C, N or O,
R$_8$, R$_9$ are independently of each other H or straight-chain or branched C$_1$-C$_{12}$ alkyl, which is unsubstituted or substituted by at least one CN, Hal, or NO₂, and wherein one or more of embedded, non-adjacent CH2 groups may independently be replaced by —O—, —CO—, —CO—O—, —CO—NR'—, —CH=CH—, —C≡C—, or a group of the formula V

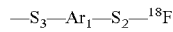  V wherein S₂, S₃ are independently of each other a single bond or a spacer unit, such as straight chain or branched C₁-C₁₂ alkyl, which is unsubstituted or substituted by at least one CN, Hal, or NO₂, and wherein one or more of the non-adjacent CH₂ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —SO₃R'—, —PR'—, or a five- or six-membered aromatic ring, which is unsubstituted or substituted with CN, Hal, NO₂, COR', or COOR', wherein R' represents H or C₁-C₆ alkyl, with the proviso that no two heteroatoms are adjacent to each other, Ar₁ is a triazole or a tetrazole, and X₁ to X₅, R₁ to R₆, m, p and q, are as defined hereinabove, with the proviso that either R₆ is a group of formula III or one of R₈ and R₉ is a group of formula V.

In a further aspect the present invention is directed to a method of their preparation. More specifically, the compounds of the invention may be obtained using a 1,3-dipolar cycloaddition of azides with alkynes or alkyne substitutes, such as nitriles in high yields.

In another aspect the present invention is directed to pharmaceutical compositions of the compounds of the invention.

In yet another aspect the present invention is directed to the use in diagnosis and monitoring of therapy of cancer and inflammatory and autoimmune diseases in vitro or in vivo.

In one embodiment, the present invention is directed towards uses of the compounds of the invention for diagnostic imaging of a cell or population of cells expressing a folate-receptor.

More specifically the present invention includes methods for diagnostic imaging of a cell or population of cells expressing a folate-receptor, which includes for example methods for in vitro detection of a cell expressing the folate receptor, for example a tumor cell or an activated macrophage, in a tissue sample. Such methods may also be performed in vivo.

Thus, in a further embodiment the present invention is directed towards uses of the compounds of the invention for convenient and effective administration to a subject in need for diagnostic imaging and/or monitoring of therapy of cancer and inflammatory and autoimmune diseases. The subject of the methods of the present invention is preferably a mammal, such as an animal or a human, preferably a human.

Such methods of the invention may be performed in combination with any other methods of diagnosis or therapy of cancer and inflammatory and autoimmune diseases including methods using other already developed diagnostic and/or therapeutic agents and utilizing x-ray computed tomography (CT), magnetic resonance imaging (MRI), functional magnetic resonance imaging (fMRI), single photon emission computed tomography (SPECT), optical imaging, and ultrasound.

Other features and advantages of the invention will be apparent from the following detailed description thereof and from the claims.

DETAILED DESCRIPTION OF THE INVENTION

Figure 1:
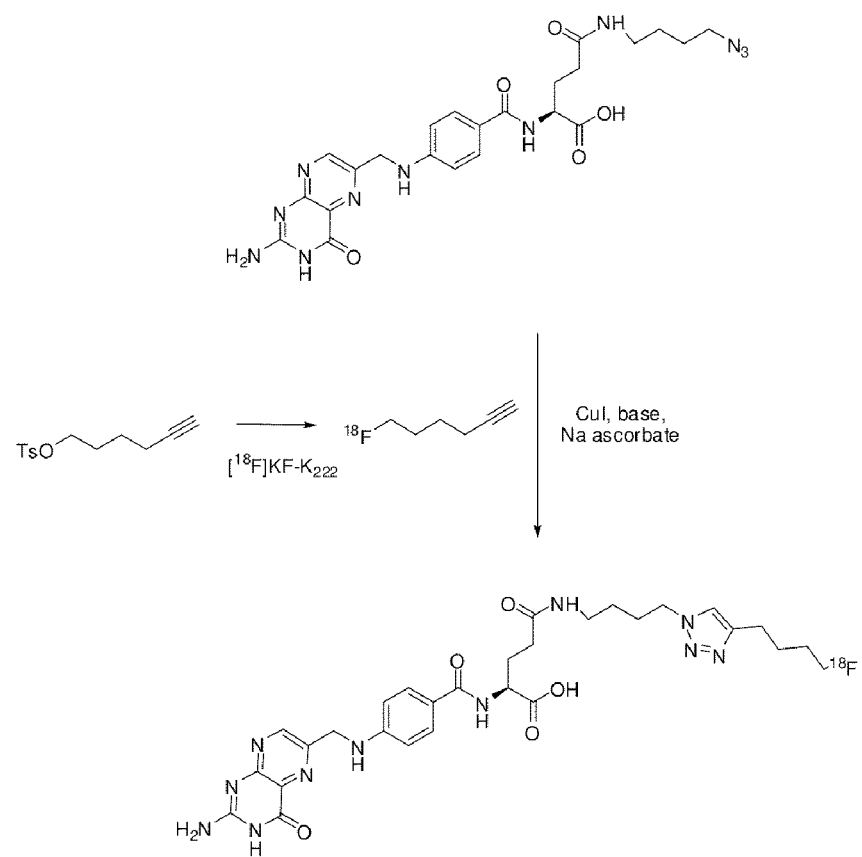
FIG. 1. Synthesis of $^{18}$F-Click folate ($\gamma$-(4-(4-(4-[$^{18}$F]fluorobutyl)-1,2,3-triazol-1-yl)butyl) folic acid amide.

The present invention is in a first aspect directed to new $^{18}$F-folate radiopharmaceuticals (hereinafter also called compounds of the invention), wherein fluorine-18 is linked through a triazole or a tetrazole linker to a folate or derivative thereof, such as to the glutamate functionality of folic acid.

The term "folate" as used herein, comprises compounds based on a condensed pyrimidine heterocycle, which is linked to an aminobenzoyl moiety carrying in para-position a group S₁ as defined hereinafter. As used herein a "condensed pyrimidine heterocycle" includes a pyrimidine fused with a further 5- or 6-membered heterocycle, such as a pteridine or a pyrrolopyrimidine bicycle. Preferred representatives of folates as used herein are based on a folate skeleton, i.e. pteroyl-glutamic acid or N-[4(pteridin-6-ylmethylamino) benzoyl]-glutamic acid), and derivatives thereof and includes optionally substituted folic acid, folinic acid, pteropolyglutamic acid, and folate receptor-binding pteridines such as tetrahydropterins, dihydrofolates, tetrahydrofolates, and their deaza and dideaza analogs. Folic acid is the preferred basic structure used for the compounds of this invention. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5-dideaza, 5,10-dideaza, 8,10-dideaza, and 5,8-dideaza analogs. Preferred deaza analogs compounds include N-[4-[2-[(6R)-2-amino-1,4,5,6,7,8-hexahydro-4-oxopyrido[2,3-d]pyrimidin-6-yl]ethyl]benzoyl]-L-glutamic acid (Lometrexol) and N-[4-[1-[(2,4-diamino-6-pteridinyl)methyl]propyl]benzoyl]-L-glutamic acid (Edatrexate).

More specifically, the new folate radiopharmaceuticals are compounds of formula I,

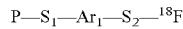  I wherein

P is a folate or derivative thereof,

S₁, S₂ are independently of each other a single bond or a spacer, and

Ar₁ is a triazole or tetrazole.

Preferably, S₁ and S₂ are independently of each other a single bond or a spacer unit, such as straight-chain or branched C₁-C₁₂ alkyl, which is unsubstituted or substituted by at least one CN, Hal, or NO₂, and wherein one or more of the non-adjacent CH₂ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —SO₃R'—, —PR'—, or a five- or six-membered aromatic ring, which is unsubstituted or substituted with CN, Hal, NO₂, COR' or COOR', wherein R' represents H or C₁-C₆ alkyl, or a combination thereof.

In another specific embodiment, the new folate radiopharmaceuticals are compounds of formula II

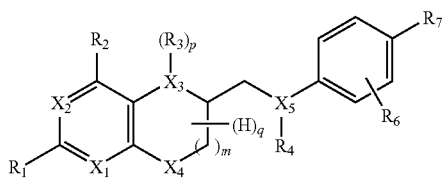

wherein
$X_1$ to $X_5$ are independently of each other C or N,
$R_1$ and $R_2$ are independently of each other H, Hal, —OR', —NHR', C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R' is H or C1-C6 alkyl,
$R_3$, $R_4$ are independently of each other H, formyl, iminomethyl, nitroso, $C_1$-$C_{12}$ alkyl, $C_1$-$C_{12}$ alkoxy, $C_1$-$C_{12}$ alkanoyl, halosubstituted $C_1$-$C_{12}$ alkanoyl,
$R_5$ is H, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, and ($C_1$-$C_{12}$ alkylamino)carbonyl,
$R_6$, $R_7$ are independently of each other straight-chain or branched $C_1$-$C_{12}$ alkyl, which is unsubstituted or substituted by at least one CN, Hal, or $NO_2$, or a group of the formula III

wherein $S_1$ and $S_2$ are independently of each other a single bond or a spacer unit, such as straight-chain or branched C1-C12 alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N═, —NR'—CO—, —CO—NR'—, —NR'—CO—O—, —O—CO—NR'—, NR'—CO—NR'—, —CH═CH—, —C≡C—, —S—, —SO₃R'—, —PR'—, or a five- or six-membered aromatic ring, which is unsubstituted or substituted with CN, Hal, $NO_2$, COR', or COOR', wherein R' represents H or $C_1$-$C_6$ alkyl, or a combination thereof, and
$Ar_1$ is a triazole or a tetrazole,
with the proviso that one of $R_6$ and $R_7$ is a group of formula III,
m is 0 or 1,
p is 0, 1 or 2, and
q has a value of 1 to 7.

In a preferred embodiment $R_6$ is CN, Hal, $NO_2$, or a group $R_5$ and $R_7$ is a group of formula III.

In another preferred embodiment $R_7$ is CN, Hal, $NO_2$, or a group $R_5$ and $R_6$ is a group of formula III.

It is understood, that the abbreviations "N" and "C" are representative for all possible degrees of saturation, i.e. N includes —NH— and —N═linkages and C includes —CH₂— and —CH═ linkages.

It is further understood, that $(H)_q$ represents all H substituents on the indicated ring (i.e. on $X_3$, C6, C7 and $X_4$). For example q=5 for a fully saturated unsubstituted analog ($X_3$=$X_4$=N, p=0) or q=7 for a fully saturated unsubstituted 5,8-dideaza analog ($X_3$=$X_4$=C, p=0) and q=1 for a fully unsaturated analog with $X_3$=$X_4$=N, p=0.

$S_1$ is preferably a single bond or a spacer unit, such as straight-chain or branched $C_1$-$C_{18}$ alkyl, which is unsubstituted or substituted by at least one CN, Hal, or $NO_2$, and wherein one or more of non-adjacent $CH_2$ groups may independently be replaced by —O—, —CO—, —CO—O—, —NR'—, —NR'—CO—, —CO—NR'—, —CH═CH—, —C≡C—, or a five- or six-membered aromatic ring, which is unsubstituted or substituted with CN, Hal, $NO_2$, COR', or COOR', wherein R' represents H or $C_1$-$C_6$ alkyl, or a combination thereof, more preferably a single bond or a spacer unit, such as straight-chain or branched $C_1$-$C_{18}$ alkyl, which is unsubstituted or substituted by at least one CN, Hal, or $NO_2$, and wherein one or more of non-adjacent $CH_2$ groups may independently be replaced by —O—, —CO—, —CO—O—, —NR'—, —NR'—CO—, —CO—NR'—, —CH═CH—, —C≡C—, or an unsubstituted five- or six-membered aromatic ring.

In a preferred embodiment, $S_1$ is a single bond or a straight-chain or branched $C_1$-$C_{12}$ alkyl, wherein one or more of non-adjacent $CH_2$ groups may independently be replaced by —O—, —CO—, —CO—O—, —NR'—, —NR'—CO—, —CO—NR'—, —CH═CH—, —C≡C—.

In another preferred embodiment $S_1$ may represent an amino acid, i.e. a compounds with both an amino group (e.g., $NH_2$ or $NH_3^+$) and a carboxylic acid group (e.g., COOH or COO). In a specific embodiment, the amino acid may be an α-amino acid, a β-amino acid, a D-amino acid or an L-amino acid. The amino acid may be a naturally occurring amino acid (e.g., alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, or histidine, etc.) or it may be a derivative thereof. Examples of derivatives include optionally substituted amino acids, e.g. having one or more substituents selected from CN, Hal, and/or $NO_2$. The amino acid may also include any other non-naturally occurring amino acids, such as e.g. norleucine, norvaline, L- or D-naphthalanine, ornithine, homoarginine and others well known in the peptide art (see for example in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference). Amino acids and amino acid analogs/derivatives can be purchased commercially (Sigma Chemical Co.; Advanced Chemtech) or synthesized using methods known in the art. In another specific embodiment, the amino acid may also be part of a polyamino acid (also termed polypeptide), wherein a plurality of same or different amino acids as defined hereinabove are covalently linked, i.e. linked through conventional peptide or other bonds. Preferred amino acids include for example glutamic acid, aspartic acid, glutamine, aspartine, lysine, arginine, cystein, and derivatives thereof and preferred polyamino acids include homopolymers the respective homopolymers thereof (i.e. polyglutamic acid, polyaspartic acid, etc). Most preferred are optionally substituted aspartic and glutamic acid.

$S_2$ is preferably a single bond or a straight-chain or branched $C_1$-$C_{12}$ alkyl, which is unsubstituted or substituted by at least one CN, Hal, or $NO_2$, or a five- or six-membered aromatic ring, which is unsubstituted or substituted with CN, Hal, $NO_2$, COR', or COOR', wherein R' represents H or $C_1$-$C_6$ alkyl, or a combination thereof, more preferably a single bond or a straight-chain or branched $C_1$-$C_{12}$ alkyl, which is unsubstituted or substituted by at least one CN, Hal, or $NO_2$.

Most preferably, $S_2$ is a single bond or a straight-chain or branched $C_1$-$C_{12}$ alkyl.

As indicated hereinabove, preferred representatives of folates as used herein are based on a folate skeleton wherein $S_1$ is a glutamic acid residue, and derivatives thereof. Thus in another specific embodiment, the new folate radiopharmaceuticals are compounds of formula IV

IV

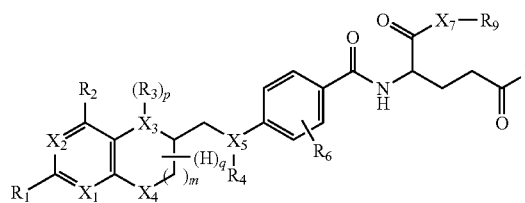

wherein
$X_6$, $X_7$ are independently of each other C, N or O,
$R_8$, $R_9$ are independently of each other H or straight chain or branched C1-C12 alkyl, which is unsubstituted or substituted by at least one CN, Hal, or NO2, and wherein one or more of embedded, non-adjacent CH2 groups may independently be replaced by —O—, —CO—, —CO—O—, —CO—NR'—, —CH=CH—, —C≡C—, or a group of the formula V $$-S_3-Ar_1-S_2-{}^{18}F \qquad V$$

wherein $S_2$, $S_3$ are independently of each other a single bond or a spacer unit, such as straight chain or branched $C_1$-$C_{12}$ alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —SO₃R'—, —PR'—, or a five- or six-membered aromatic ring, which is unsubstituted or substituted with CN, Hal, $NO_2$, COR', or COOR', wherein R' represents H or $C_1$-$C_6$ alkyl, or a combination thereof,
$Ar_1$ is a triazole or a tetrazole, and
$X_1$ to $X_5$, $R_1$ to $R_6$, m, p and q, are as defined according to compound of formula II and preferred embodiments as defined hereinafter,
with the proviso that either $R_6$ is a group of formula III or one of $R_8$ and $R_9$ is a group of formula V.

$S_2$ and $S_3$ are preferably independently of each other a single bond or a straight chain or branched $C_1$-$C_{12}$ alkyl, which is unsubstituted or substituted by at least one CN, Hal, or $NO_2$, or a five- or six-membered aromatic ring, which is unsubstituted or substituted with CN, Hal, $NO_2$, COR', or COOR', wherein R' represents H or $C_1$-$C_6$ alkyl, or a combination thereof, more preferably straight chain or branched $C_1$-$C_{12}$ alkyl, which is unsubstituted or substituted by at least one CN, Hal, or $NO_2$.

Most preferably $S_2$ and $S_3$ are independently of each other a single bond or a straight chain or branched $C_1$-$C_{12}$ alkyl.

$Ar_1$ is a triazole or tetrazole of formula V-a and V-b

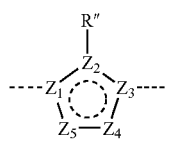

V-a

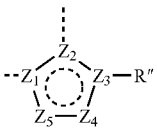

V-b wherein the dotted lines represent linking sites to the spacer groups, and
$Z_1$ to $Z_5$ are independently of each other C or N, such that sum of all N is 3 or 4,
and is preferably selected from formulae V-c, V-d, and V-e

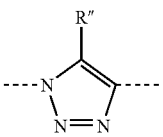

V-c

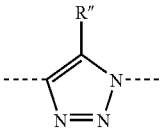

V-d

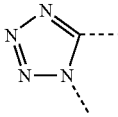

V-e wherein the dotted lines represent linking sites to the spacer groups and R" is H, Hal, NH—COR', NH—$SO_2$R', $CO_2$R', COR', or straight chain or branched $C_1$-$C_{12}$ alkyl, which is unsubstituted or substituted by at least one CN, Hal, OH, $NH_2$, $SO_3H$, SH, $CO_2H$, or $NO_2$, or a five- or six-membered aromatic ring, which is unsubstituted or substituted with CN, Hal, $NO_2$, COR', or COOR', wherein R' represents H or $C_1$-$C_6$ alkyl.

In a specific embodiment $R_6$ is CN, Hal, $NO_2$, or a group $R_5$ and one of $R_8$ and $R_9$ is a group of formula V.

In another specific embodiment $R_6$ is CN, Hal, $NO_2$, or a group $R_5$, H or is straight chain or branched $C_1$-$C_{12}$ alkyl, which is unsubstituted or substituted by at least one CN, Hal, or $NO_2$, and $R_9$ is a group of formula V.

In a further specific embodiment $R_6$ is CN, Hal, $NO_2$, or a group $R_5$, $R_9$ is H or straight chain or branched $C_1$-$C_{12}$ alkyl, which is unsubstituted or substituted by at least one CN, Hal, or NO2, and wherein one or more of embedded, non-adjacent CH2 groups may independently be replaced by —O—, —CO—, —CO—O—, —CO—NR'—, —CH=CH—, —C≡C—, and $R_8$ is a group of formula V.

In a further specific embodiment $R_8$ and $R_9$ are independently of each other H or straight chain or branched $C_1$-$C_{12}$ alkyl, which is unsubstituted or substituted by at least one CN, Hal, or NO2, and wherein one or more of embedded, non-adjacent CH2 groups may independently be replaced by —O—, —CO—, —CO—O—, —CO—NR'—, CH=CH—, —C≡C—, and $R_6$ is a group of formula V.

Thus, in another specific embodiment, the new folate radiopharmaceuticals are compounds of formulae VI, VIa or VIb,

VI

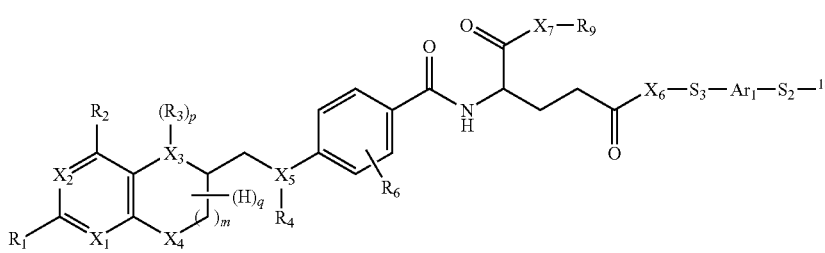

VIa

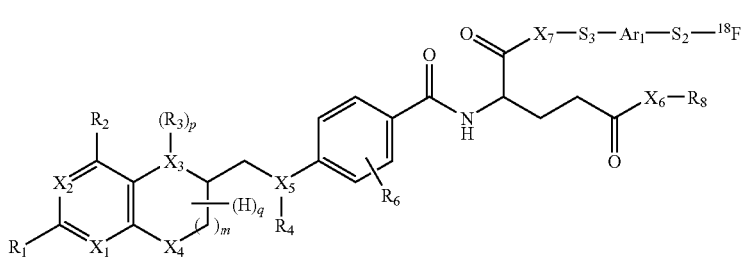

VIb

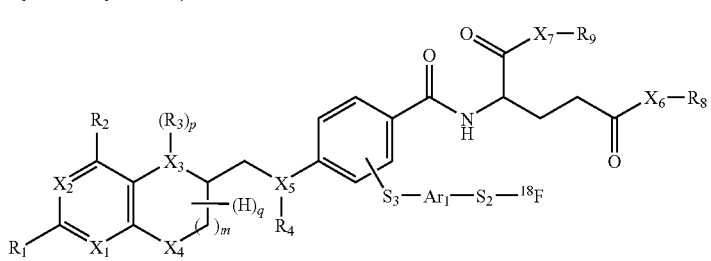

wherein
$X_1$ to $X_5$ are independently of each other C or N,
$X_6$, $X_7$ are independently of each other C, N or O,
$R_1$ and $R_2$ are independently of each other H, Hal, —OR', —NHR', C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R' is H or C1-C6 alkyl,
$R_3$, $R_4$ are independently of each other H, formyl, iminomethyl, nitroso, C1-C12 alkyl, C1-C12 alkoxy, C1-C12 alkanoyl, halosubstituted C1-C12 alkanoyl,
$R_6$ is H, CN, Hal, $NO_2$, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, or ($C_1$-$C_{12}$ alkylamino)carbonyl,
$R_8$, $R_9$ are independently of each other H or straight chain or branched C1-C12 alkyl, which is unsubstituted or substituted by at least one CN, Hal, or NO2, and wherein one or more of embedded, non-adjacent CH2 groups may independently be replaced by —O—, —CO—, —CO—O—, —CO—NR'—, —CH═CH—, —C≡C—,
$S_2$, $S_3$ are independently of each other a single bond or a spacer unit, such as straight-chain or branched $C_1$-$C_{12}$ alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N═, —NR'—CO—, —CO—NR'—, —NR'—CO—O—, —O—CO—NR'—, —NR'—CO—NR'—, —CH═CH—, —C≡C—, —S—, —$SO_3$R'—, —PR'—, or a five- or six-membered aromatic ring, which is unsubstituted or substituted with CN, Hal, $NO_2$, COR', or COOR', wherein R' represents H or $C_1$-$C_6$ alkyl, or a combination thereof,
$Ar_1$ is a triazole or a tetrazole,
m is 0 or 1,
p is 0, 1 or 2, and
q has a value of 1 to 7.

$S_2$ and $S_3$ are preferably independently of each other a single bond or a straight-chain or branched $C_1$-$C_{12}$ alkyl, which is unsubstituted or substituted by at least one CN, Hal, or $NO_2$, or a five- or six-membered aromatic ring, which is unsubstituted or substituted with CN, Hal, $NO_2$, COR', or COOR', wherein R' represents H or $C_1$-$C_6$ alkyl, or a combination thereof, more preferably straight-chain or branched $C_1$-$C_{12}$ alkyl, which is unsubstituted or substituted by at least one CN, Hal, or $NO_2$.

Most preferably, $S_2$ and $S_3$ are independently of each other a single bond or a straight chain or branched $C_1$-$C_{12}$ alkyl.

In a further specific embodiment, the new folate radiopharmaceuticals are compounds of formulae VIIa to VIIf or VIIIa to VIIIf, VIIa

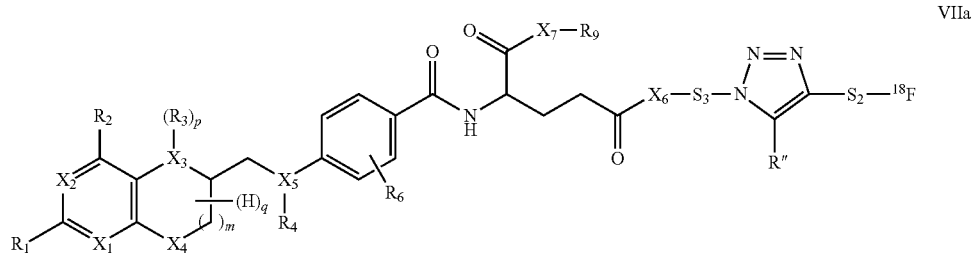

-continued
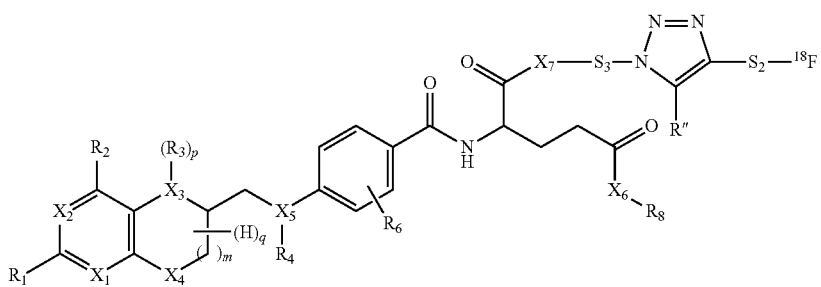
VIIb
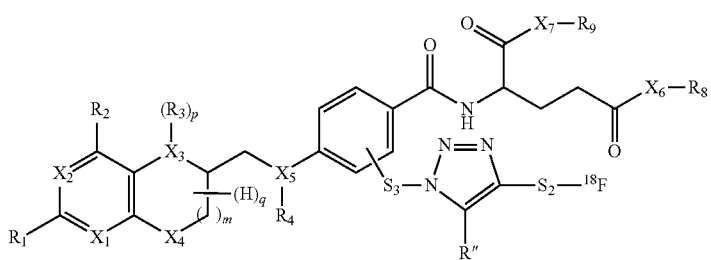
VIIc
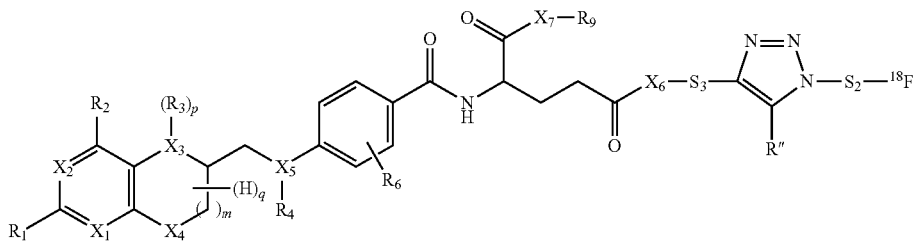
VIId
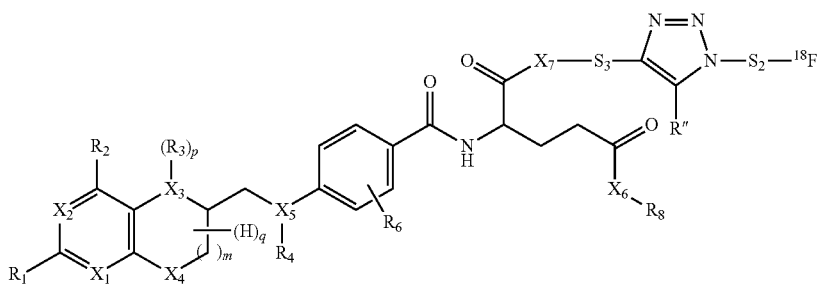
VIIe
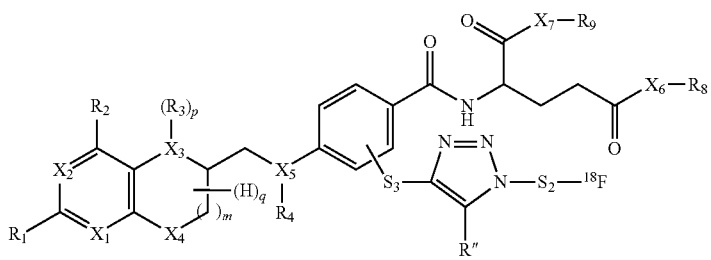
VIIf
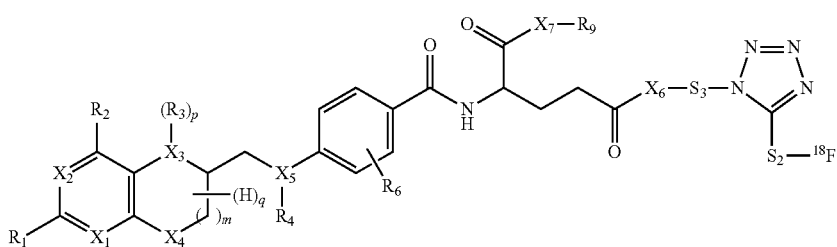
VIIIa -continued
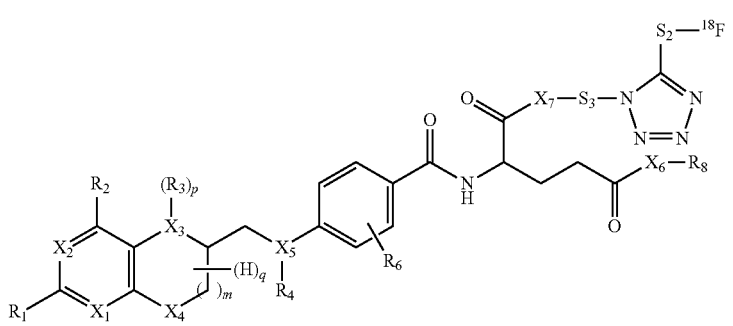
VIIIb
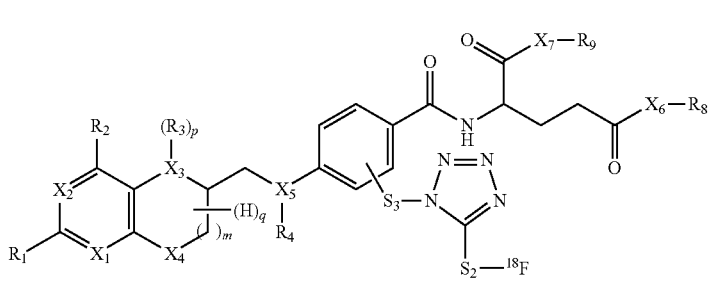
VIIIc
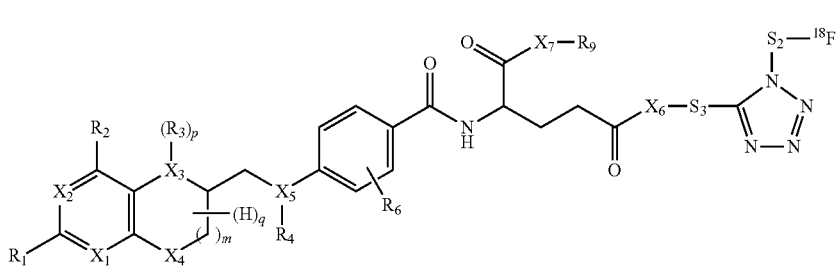
VIIId
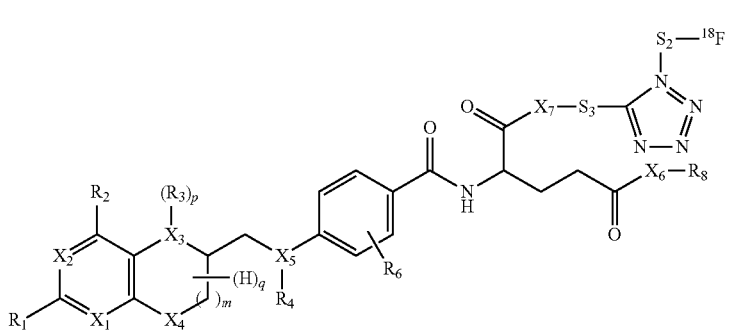
VIIIe
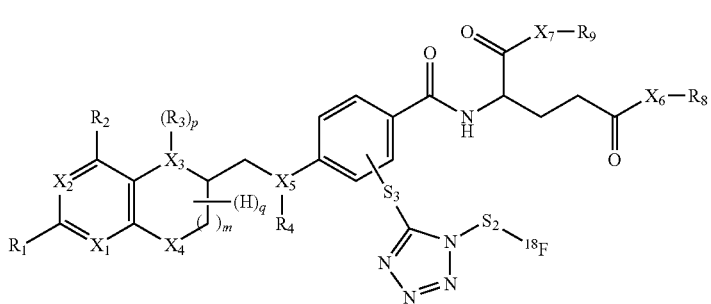
VIIIf wherein $X_1$ to $X_5$ are independently of each other C or N, $X_6$, $X_7$ are independently of each other C, N or O, $R_1$ and $R_2$ are independently of each other H, Hal, —OR', —NHR', C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R' is H or C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_6$ is H, CN, Hal, $NO_2$, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, or ($C_1$-$C_{12}$ alkylamino)carbonyl, $R_8$, $R_9$ are independently of each other H or straight chain or branched $C_1$-$C_{12}$ alkyl, which is unsubstituted or substituted by at least one CN, Hal, or NO2, and wherein one or more of embedded, non-adjacent CH2 groups may independently be replaced by —O—, —CO—, —CO—O—, —CO—NR'—, —CH=CH—, —C≡C—, $S_2$, $S_3$ are independently of each other a single bond or a spacer unit, such as straight-chain or branched $C_1$-$C_{12}$ alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —$SO_3$R'—, —PR'—, or a five- or six-membered aromatic ring, which is unsubstituted or substituted with CN, Hal, $NO_2$, COR', or COOR', wherein R' represents H or $C_1$-$C_6$ alkyl, or a combination thereof, R" is H, Hal, NH—COR', NH—$SO_2$R', $CO_2$R', COR', or straight-chain or branched $C_1$-$C_{12}$ alkyl, which is unsubstituted or substituted by at least one CN, Hal, OH, $NH_2$, $SO_3$H, SH, $CO_2$H, or $NO_2$, or a five- or six-membered aromatic ring, which is unsubstituted or substituted with CN, Hal, $NO_2$, COR', or COOR', wherein R' represents H or $C_1$-$C_6$ alkyl, m is 0 or 1, p is 0, 1 or 2, and q has a value of 1 to 7.

Further preferred embodiments as defined hereinabove apply also to compounds of formulae VI to VIII.

Preferably, $R_1$ and $R_2$ may independently of each other H, alkyl, —$OR_5$, —NHR', more preferably —OR', —NHR', wherein R' represents H or $C_1$-$C_6$ alkyl.

Preferably, $R_3$ is H, formyl, $C_1$-$C_{12}$ alkyl or $C_1$-$C_{12}$ alkanoyl.

Preferably, $R_4$ is H, nitroso, $C_1$-$C_{12}$ alkoxy, or $C_1$-$C_{12}$ alkanoyl.

Preferably, $R_5$ is H, $C_1$-$C_{12}$ alkyl, $C_1$-$C_{12}$ alkoxy, $C_1$-$C_{12}$ alkanoyl, ($C_1$-$C_{12}$ alkoxy)carbonyl, or ($C_1$-$C_{12}$ alkylamino) carbonyl, more preferably H or $C_1$-$C_4$ alkyl.

Preferably, $R_6$ is H, CN, Hal, $NO_2$, $C_1$-$C_{12}$ alkyl, $C_1$-$C_{12}$ alkoxy, $C_1$-$C_{12}$ alkanoyl, or ($C_1$-$C_{12}$ alkoxy)carbonyl, more preferably H, CN, Hal, $NO_2$, or $C_1$-$C_8$ alkyl.

One specific embodiment of the compounds of the invention includes for example compounds wherein (a) $X_1$ to $X_5$ are N, $R_1$ is $NY_1Y_2$, $R_2$ is O, $R_4$ is $Y_3$, m is 1, p is 0 or 1 and q is 1 or 3, or (b) $X_1$ to $X_5$ are N, $R_1$ is $NY_1Y_2$, $R_2$ is $NH_2$, $R_4$ is $Y_3$, m is 1, p is 0 and q is 1.

Thus, in a further specific embodiment the present invention is for example directed to compounds of formulae IX, IXa, X or Xa,

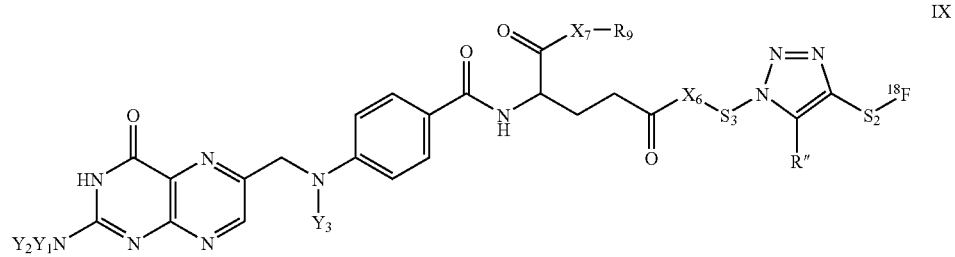

IX

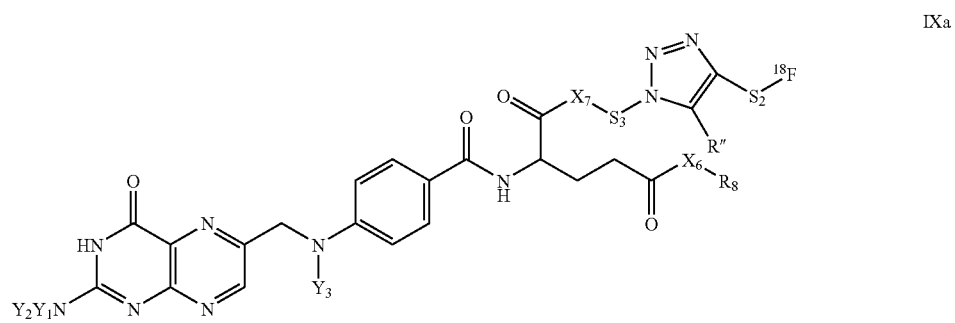

IXa

-continued

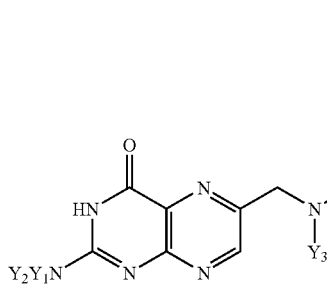
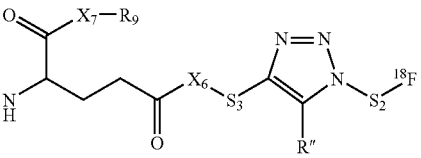

X

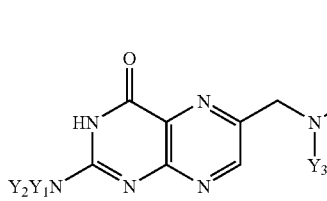

Xa wherein, $X_6$, $X_7$ are independently of each other C, N or O, $Y_1$, $Y_2$ are independently of each other selected from H, formyl, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, $Y_3$ is selected from H, formyl, nitroso, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, $R_8$, $R_9$ are independently of each other H or straight chain or branched C1-C12 alkyl, which is unsubstituted or substituted by at least one CN, Hal, or NO2, and wherein one or more of embedded, non-adjacent CH2 groups may independently be replaced by —O—, —CO—, —CO—O—, —CO—NR'—, —CH=CH—, —C≡C—, R" is H, Hal, NH—COR', NH—$SO_2$R', $CO_2$R', COR', or straight-chain or branched $C_1$-$C_{12}$ alkyl, which is unsubstituted or substituted by at least one CN, Hal, OH, $NH_2$, $SO_3$H, SH, $CO_2$H, or $NO_2$, or a five- or six-membered aromatic ring, which is unsubstituted or substituted with CN, Hal, $NO_2$, COR', or COOR', wherein R' represents H or $C_1$-$C_6$ alkyl, and $S_2$, $S_3$ are independently of each other a single bond or a spacer unit, such as straight-chain or branched $C_1$-$C_{12}$ alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —$SO_3$R'—, —PR'— or a five- or six-membered aromatic ring, which is unsubstituted or substituted with CN, Hal, $NO_2$, COR', or COOR', wherein R' represents H or $C_1$-$C_6$ alkyl, or a combination thereof.

Preferably R" is H, Hal, NH—COR', NH—$SO_2$R', $CO_2$R', COR', or straight-chain or branched $C_1$-$C_{12}$ alkyl, which is unsubstituted or substituted by at least one CN, Hal, OH, $NH_2$, $SO_3$H, SH, $CO_2$H, or $NO_2$.

The term "alkyl", when used singly or in combination, refers preferably to straight chain or branched alkyl groups containing 1 to 12 carbon atoms, such as methyl, ethyl, propyl, isopropyl, butyl, sec-butyl, isobutyl, t-butyl, pentyl, isopentyl, neopentyl, hexyl, heptyl, octyl, nonyl, decyl, undecyl, dodecyl and the like. More preferred alkyl groups contain 1 to 8, more preferably 1 to 4 carbon atoms.

As used herein, the term "alkenyl", singly or in combination with other groups, refers to straight chain or branched alkyl groups containing 2 to 12 carbon atoms, such as methylene, ethylene, propylene, isopropylene, butylene, t-butylene, sec-butylene, isobutylene, amylene, isoamylene, pentylene, isopentylene, hexylene and the like. The preferred alkenyl groups contain 2 to 6 carbon atoms.

The term "alkynyl" as used herein refers to a linear or branched chain of carbon atoms with one or more carbon-carbon triple bonds. The preferred alkynyl groups contain 2 to 12, more preferably 2 to 6 carbon atoms.

The term "alkoxy" as used herein refers to alkyl, as defined above, substituted with oxygen, such as methoxy, ethoxy, propoxy, isopropoxy, butoxy, tert-butoxy and the like.

The term "alkanoyl" as used herein refers to formyl, or alkyl, as defined above, terminally-substituted with a carbonyl such as acetyl, propanoyl, butanoyl, pentanoyl and the like.

The term "alkylamino" as used herein refers to alkyl, as defined above, substituted with nitrogen, including both monoalkylamino such as methylamino, ethylamino, propylamino, tert-butylamino, and the like, and dialkylamino such as dimethylamino, diethylamino, methylpropylamino, and the like.

The term "halo" as used herein refers to any Group 17 element and includes fluoro, chloro, bromo, iodo, and astatine (o).

In a further aspect the present invention provides a method of synthesizing a compound of the invention. Applicants have found that the compounds of the invention may be obtained in an effective manner by a process which comprises a cycloaddition of an azide with an alkyne or alkyne substitute under thermal conditions or in the presence of a catalyst. These reactions are known as Huisgen 1,3-dipolar cycloaddition (thermal conditions) and Click-Reaction (catalytic conditions) and have been described in the art (Kolb and Sharpless, *Drug Discovery Today* 2003, 8, 1128; Kolb et al. *Angew. Chem. Int. Ed.* 2001, 40, 2004; Rostovtsev, V. V. et al. *Angew. Chem. Int. Ed.* 2002, 41, 2596; US 2005/02222427; WO 06/116629). More specifically compounds of formula I wherein $Ar^1$ is a triazole are obtained by cycloaddition of an azide $R_a$—$N_3$ with an alkyne $R_b$—C≡C—$R_c$ and compounds of formula I wherein $Ar^1$ is a tetrazole are obtained by cycloaddition of an azide $R_a$—$N_3$ with a cyanide $R_b$—C≡N. All possible combinations are contemplated herein, i.e. $R_a$ being the folate derivative and $R_b$ being the $^{18}$F-labelled group as well as $R_b$ being the folate derivative and $R_a$ being the $^{18}$F-labelled group. Thus the modular and versatile nature of the reaction allows employing a wide variety of linkers to couple the radioisotope to folic acid.

In one specific embodiment the cycloaddition is performed under thermal conditions, i.e. at temperatures ranging from 10 to 200° C., preferably from 10 to 100° C.

In another embodiment the cycloaddition is performed in the presence of a catalyst, such as a transition metal complex, such as Ru and Cu(I). Preferred catalysts are Cu(I) salts, such as Cu(I) chloride, bromide, iodide. Alternatively Cu(I) can be obtained by in situ reduction of a Cu(II) salt. This reaction can be performed in a variety of protic or aprotic solvents, such as for example methanol, ethanol, 2-propanol, tertiary-butanol, n-butanol and/or water or buffered solutions thereof, at a wide range of temperatures (such as between 10 and 100° C., preferably room temperature) and varying pH (such as from 4 to 12), under oxidative or reducing conditions and in the presence of other functional groups with no need for protecting groups.

It will be obvious for a skilled person to select appropriate conditions (see also US 2005/0222427 which is incorporated herein by reference as well as references cited therein).

The $^{18}$F-labelled starting material, i.e. the $^{18}$F-labelled alkyne, alkyne substitute or azide, for the cycloaddition reaction is obtained in a displacement reaction with the respective alkyne, alkyne substitute or azide having a suitable leaving group. The leaving group on the alkyne may be any common leaving group known in the art and includes for example halogen, nitro, diazonium salts, sulfonate esters, including mesylate, tosylate, pentafluorobenzoate, and the like. Typically, the displacement reaction is performed in a polar aprotic solvent selected from acetonitrile, acetone, 1,4-dioxane, tetrahydrofuran (THF), N-methylpyrrolidinone (NMP), dimethoxyethane (DME), dimethylacetamide (DMA), N,N-dimethylformamide (DMF), dimethylsulfoxide (DMSO) and hexamethylphosphoramide (RMPA) and mixtures thereof.

Thus in one exemplary reaction, an alkyne or alkyne substitute of choice, provided with a suitable leaving group, was labelled with a [$^{18}$F] fluoride activated by phase transfer catalysts such as tetrabutylammonium carbonate or aminopolyethers (e.g. Kryptofix© 2.2.2) in combination with potassium carbonate or oxalate in a displacement reaction under standard conditions (for example acetonitrile, 100° C., 10-15 min). The obtained [$^{18}$F]-labelled alkyne was co-distilled with a suitable solvent to a catalyst of choice (e.g. Cu(I)I). To this mixture the azido-folic acid or derivative of choice was added under standard conditions (for example Na ascorbate in DMF, H$_2$O and DIPEA at 80° C.) to give the final labelled product with a RCY of 25-35%.

Alternatively, an azide of choice, provided with a suitable leaving group, was labelled with a [$^{18}$F]fluoride activated by phase transfer catalysts such as tetrabutylammonium carbonate or aminopolyethers (e.g. Kryptofix© 2.2.2) in combination with potassium carbonate or oxalate to give the [$^{18}$F]-labelled azide, which was subsequently coupled to the alkyne substituted folic acid or derivative of choice in a catalyzed 1,3-dipolar cycloaddition under standard conditions.

In a further aspect the present invention provides uses of folate radiopharmaceuticals of the invention for convenient and effective administration to a subject in need for diagnostic imaging.

Thus the present invention provides a method for diagnostic imaging of a cell or population of cells expressing a folate-receptor, said method comprising the steps of administering at least one folate radiopharmaceutical of the invention in a diagnostic imaging amount, and obtaining a diagnostic image of said cell or population of cells.

Such imaging may be performed on a cell or population of cells expressing a folate-receptor in vitro or in vivo.

Thus, the present invention provides a method for in vitro detection of a cell expressing the folate receptor in a tissue sample which includes contacting said tissue sample with at least one folate radiopharmaceutical of the invention in effective amounts and for sufficient time and conditions to allow binding to occur and detecting such binding by PET imaging.

In a further aspect the present invention provides uses of folate radiopharmaceuticals of the present invention for convenient and effective administration to a subject in need for diagnostic imaging or monitoring of therapy of cancer and inflammatory and autoimmune diseases.

In another aspect the present invention provides a method for simultaneous diagnosis and therapy, comprising the steps of administering to a subject in need thereof at least one folate radiopharmaceutical of the present invention in a diagnostically effective amount in combination with a therapeutically active, and obtaining a diagnostic image of said tissues to follow the course of treatment.

The subject of the methods of the present invention is preferably a mammal, such as an animal or a human, preferably a human.

The dosage depends on the nature of the effect desired, such as the form of diagnosis or therapy, on the kind and frequency of treatment, on the diagnostic instrumentation, on the form of application of the preparation, and on the age, weight, nutrition and condition of the recipient, kind of concurrent treatment, if any.

However, the most preferred dosage can be tailored to the individual subject, as is understood and determinable by one of skill in the art, without undue experimentation. This typically involves adjustment of a standard dose, e.g., reduction of the dose if the patient has a low body weight.

Treatment can commence with a smaller amount, below the optimum amount, which can be increased in order to achieve the optimum effect.

The imaging procedure in the PET scanner takes place from within minutes to 2-4 hours after administration of the radiotracer. The schedule depends on the imaging target and kinetics of the radiotracer as well as the desired information.

The preferred route of administration of the folate radiopharmaceuticals of the present invention is by intravenous injection.

The suitable forms for injection include sterile aqueous solutions or dispersions of the above mentioned folate radiopharmaceuticals of the present invention. Typically the radiopharmaceutical will be formulated in physiological buffer solutions.

The folate radiopharmaceuticals can undergo sterilization by any art recognized technique, including but not limited to, addition of antibacterial of antifungal agents, for example, paraben, chlorobutanol, phenol, sorbic acid, thimerosal, and the like. Preferably they undergo a sterile filtration before administration eliminating the need of additional sterilisation agents.

For a solution to be injected a preferred unit dosage is from about 0.01 mL to about 10 mL. After intravenous administration, imaging of the organ or tumor in vivo can take place, if desired, from within minutes to 2-4 hours after the radiolabeled reagent has been administered to a subject to allow a sufficient amount of the administered dose to accumulate in the targeted area of choice.

The folate radiopharmaceuticals of the invention may also be used for in vitro detection of a cell expressing the folate receptor in a tissue biopsy taken from a subject. Thus in a further embodiment the present invention provides a method for in vitro detection of a cell expressing the folate receptor, e.g. a tumor cell, in a tissue sample which includes contacting said tissue sample with a folate radiopharmaceutical of the present invention in effective amounts and for sufficient time and conditions to allow binding to occur and detecting such binding by imaging techniques.

Samples can be collected by procedures known to the skilled person, e.g., by collecting a tissue biopsy or a body fluid, by aspirating for tracheal or pulmonary samples and the like.

Tissue samples to be tested include any tissue suspected to contain a cell expressing a folate receptor, such as tumour cells, epithelial cells, kidneys, gastrointestinal or the hepatobiliary system, and others. Samples can be sectioned, e.g., with a microtome, to facilitate microscopic examination and observation. Samples can also be fixed with an appropriate fixative either before or after incubation with one of the folate radiopharmaceuticals of the present invention to improve the histological quality of sample tissues.

Time and conditions sufficient for binding of a folate radiopharmaceutical of the present invention to a folate receptor on the cell include standard tissue culture conditions, i.e. samples can be cultured in vitro and incubated with one of the complexes or compositions of the present invention in physiological media. Such conditions are well known to the skilled person. Alternatively, samples can be fixed and then incubated with a folate radiopharmaceutical of the present invention in an isotonic or physiological buffer.

For all applications it is convenient to prepare the compounds of the present invention at, or near, the site where they are to be used.

All of the compounds and/or methods disclosed and claimed herein can be made and executed without undue experimentation in light of the present disclosure. It will be apparent to those of skill in the art that variations may be applied to the present invention without departing from the scope of the invention. The Examples provided herein are intended to be illustrative and are not exhaustive; therefore the illustrated Examples should not be viewed as limiting the invention in any way.

EXAMPLES

Materials and Methods

Infrared spectra were recorded on a Jasco FT/IR-6200 ATR-IR. Nuclear magnetic resonance spectra were recorded with a Bruker 400 MHz or 500 MHz spectrometer with the corresponding solvent signals as an internal standard. Chemical shifts are reported in parts per million (ppm) relative to tetramethylsilane (0.00 ppm). Values of the coupling constant, J, are given in Hertz (Hz); the following abbreviations are used in the experimental section for the description of $^1$H-NMR spectra: singlet (s), doublet (d), triplet (t), multiplet (m), doublet of doublets (dd). The chemical shifts of complex multiplets are given as the range of their occurrence. Low resolution mass spectra (LR-MS) were recorded with a Micromass Quattro micro™ API LC-ESI. Water sensitive reactions were run under argon in flame-dried glass ware. Reactions were monitored by thin layer chromatography (TLC, performed on EM Science 0.25 mm thick, precoated silica gel 60 F-254 glass supported plates) or HPLC. HPLC was performed on a Merck-Hitachi L-7000 system equipped with an L-7400 tunable absorption detector. Analytical HPLC was performed with an XBridge® column (C18, 5 μm, 4.6× 150 mm, Waters) using the following solvent system (1 mL/min): 0.1% TFA$_{aq}$ (solvent A), acetonitril (solvent B), 1 mL/min; 0-1 min, 95% A; 1-15 min, 95→5% A; 15-20 min, 5% A; 20→22 min, 5→95% A; 22→25 min, 95% A. Semi-prep HPLC was performed with XBridge® semiprep column (C18, 5 μm, 10×150 mm, Waters), 3 mL/min, isochratic NH$_4$HCO$_3$ (10 mM, 88%)/CH$_3$CN (12%). All chemicals were used as supplied unlike stated otherwise.

Production of n.c.a. [$^{18}$F]fluoride N.c.a. [$^{18}$F]fluoride was produced via the $^{18}$O(p,n)$^{18}$F nuclear reaction at a Cyclone 18/9 cyclotron (IBA, Belgium). Isotopically 97% enriched [$^{18}$O]water was irradiated by a 16 MeV proton beam using a 2.1 ml liquid target. The [$^{18}$F]fluoride/[$^{18}$O]water solution was transferred from the target to a manipulator equipped syntheses hotcell using a helium stream.

[$^{18}$F]fluoride (~20-30 GBq) was trapped on an anion exchange cartridge (Sep-Pak® Light Accell Plus QMA, Waters AG), preconditioned with 5 ml 0.5M potassium carbonate solution and 5 ml water, while the [O]water was recovered for recycling. The [$^{18}$F]fluoride was directly eluted into a 10 ml sealed reaction vessel using a solution of potassium carbonate (2 mg) and Kryptofix© 2.2.2 (10 mg) in 1.5 ml acetonitrile/water (4:1). At 85-90° C. the solvents were removed by vacuum and a stream of nitrogen. Subsequently, 1 ml of dry acetonitrile was added three times and evaporated to dryness.

Example 1

Synthesis of $^{19}$F-Click Folate Standard

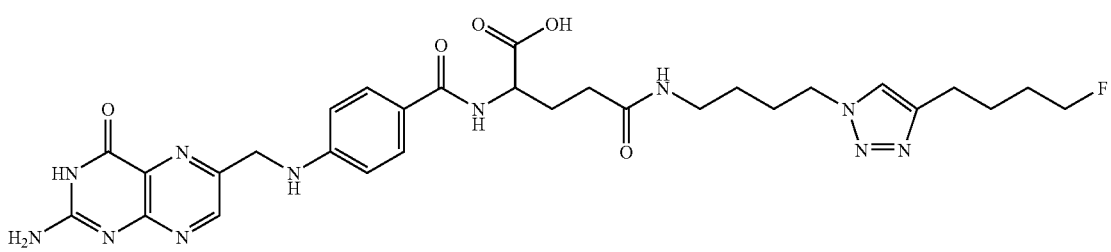

(a) Synthesis of 6-[$^{19}$F]fluoro-1-hexyne 5-hexyn-1-yl p-tosylate (330 mg, 1.3 mmol) (prepared by tosylation of 5-hexyne-1-ol according to the procedure described by van Hest et al. J. Am. Chem. Soc. 2000, 122, 1282), Kryptofix® 2.2.2 (620 mg, 1.6 mmol) and KF (97 mg, 1.6 mmol) in dry THF (12 mL) were stirred at reflux for 20 hours. Fractionated distillation of the volatile components at ambient pressure gave 6-[$^{19}$F]fluoro-1-hexyne as a 42% solution in THF (200 mg, 62%): Bp: 65-70° C./1 atm.; $^1$H-NMR (CDCl$_3$) δ 4.51 (t, 1H, J=6.0 Hz), 4.40 (t, 1H, J=6.0 Hz), 2.23 (dt, 2H, J=7.6 and 2.8 Hz), 1.95 (t, 1H, J=2.8 Hz), 1.80-1.73 (m, 2H), 1.65-1.61 (m, 2H) ppm.

(b) Synthesis of γ-(4-azido-butionyl)-folic acid amide

Figure 2:
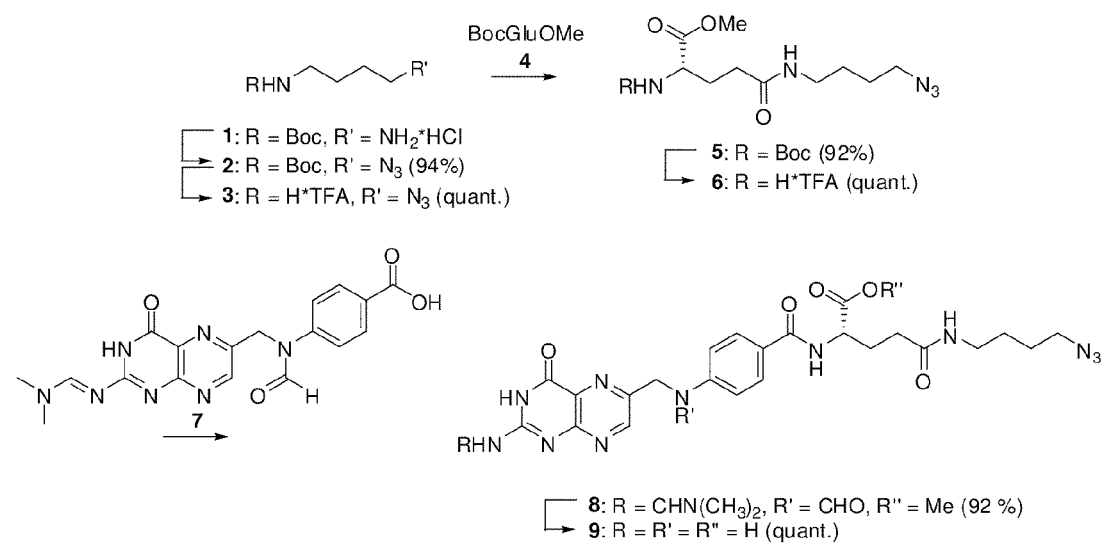
FIG. 2. Synthesis of $\gamma$-(4-azido-butionyl)-folic acid amide.

References numbers see FIG. 2.

N—BOC-amino-butane-azide (2) was prepared from mono-BOC-diaminobutane (1) according to the procedure described by Link et al. (*J. Am. Chem. Soc.* 2004, 126, 10598). Deprotection of the intermediate 2 in CH$_2$Cl$_2$/TFA (20%) at room temperature over night yielded, after drying in-vacuo, the TFA salt of 4-azido-butane-amine (3) as a colorless oil (0.44 g, 94%): $^1$H-NMR (CDCl$_3$) δ 4.54 (bs, 1H), 3.27 (t, 2H, J=6.5 Hz), 3.25-3.10 (m, 2H), 1.63-1.50 (m, 4H), 1.14 (s, 9H) ppm; LR-MS: [M+H]$^+$=215.21 (calc. for C$_9$H$_{18}$N$_4$O$_2$: 214.26).

In a flamed-dried flask under argon was dissolved BocGlu-OMe (4, 261 mg, 1.0 mmol) in dry DMF (5 mL, over molecular sieves 4 Å) and Et$_3$N (210 µL, 1.5 equiv) was added. HBTU (380 mg, 1.0 mmol) was added at 0° C. and the mixture was stirred for half an hour. The solution of the activated acid was transferred via cannula to a solution of amine TFA salt 3 (228 mg, 1.0 mmol) in dry DMF (5 mL) containing Et$_3$N (210 µL, 1.5 equiv) at 0° C. After 2 hrs, the mixture was warmed to rt and stirred over night. Removal of volatile components under reduced pressure and purification of the residue by flash chromatography on silicagel with CH$_2$Cl$_2$/MeOH (60:1 to 30:1) provided product 5 as a colorless oil (330 mg, 92%). Intermediate 5 was deprotected in CH$_2$Cl$_2$/TFA (20%) at room temperature over night yielding, after drying in-vacuo, the TFA salt of Glu(4-azido-butylamide)OMe (6) as a pale yellow oil (740 mg, quantitative): $^1$H-NMR (CDCl$_3$) δ 10.15-8.60 (bs, 3H), 6.74 (t, 1H, J=5.6 Hz), 4.14 (dd, 1H, J=7.7 and 3.7 Hz), 3.80 (s, 3H), 3.31-3.26 (m, 2H), 3.25-3.18 (m, 2H), 2.59-2.45 (m, 2H), 2.38-2.27 (m, 1H), 2.24-2.13 (m, 1H), 1.63-1.50 (m, 4H) ppm; LR-MS: [M+H]$^+$=258.23 (calc. for C$_{10}$H$_{19}$N$_5$O$_3$: 257.29).

In a flamed-dried flask under argon was suspended N2-N,N-dimethylaminomethylene-10-formyl-pteroic acid 7 (198 mg, 0.5 mmol) in dry DMF (10 mL, over molecular sieves 4 Å) and Et$_3$N (104 µL, 0.75 mmol) was added. HBTU (380 mg, 0.5 mmol) was added at 0° C. and the mixture was stirred for one hour. To the resulting orange solution was added at 0° C. a solution of amine TFA salt 6 (186 mg, 0.5 mmol) in dry DMF (9 mL) containing Et$_3$N (210 µL, 1.5 mmol). The resulting clear yellow solution was stirred at 0° C. for one hour and then allowed to warm to rt. Removal of volatile components under reduced pressure and purification of the residue by flash chromatography on silicagel with CH$_2$Cl$_2$/MeOH (17:1 to 10:1) provided product 8 as a yellow solid (290 mg, 92%).

Azido folate 8 (63 mg, 0.1 mmol) was dissolved in 1 M NaOH (3 mL) and stirred at rt over night. The resulting turbid solution was cleared by filtration through Celite™. The pH of the yellow solution was adjusted to pH ~2 by addition of HCl (first 37% HCl, then 1 M HCl) which resulted in precipitation of the product. The suspension was centrifuged (10 min at 3500 rpm), the pale yellow supernatant decanted and the solid product dried under reduced pressure to give the penta-hydrochloride salt of γ-(4-azido-butionyl)-folic acid amide 9 as a yellow powder (75 mg, quantitative): mp>200° C.; $^1$H-NMR (DMSO-d6) δ 12.21-11.95 (bs, 1H), 8.64 (s, 1H), 8.18 (d, 1H, J=7.2 Hz), 7.85 (t, 1H, J=5.7 Hz), 7.65 (d, 2H, J=9.0 Hz), 7.00-6.82 (bs, 2H), 6.93 (t, 1H, J=6.2 Hz), 6.64 (d, 2H, J=9.0 Hz), 4.49 (d, 2H, J=5.9 Hz), 4.32-4.22 (m, 1H), 3.29 (t, 2H, J=6.8 Hz), 3.03 (q, 2H, J=6.5 Hz), 3.09-2.96 (m, 2H), 2.12-1.83 (m, 2H), 1.55-1.45 (m, 2H), 1.45-1.35 (m, 2H) (one NH not observed) ppm; $^{13}$C-NMR (DMSO-d6) δ 173.8, 171.5, 166.3, 160.8, 156.6, 153.8, 150.8, 148.7, 148.5, 128.9, 127.9, 121.3, 111.2, 52.2, 50.3, 45.9, 37.9, 32.0, 26.6, 26.3, 25.7 ppm; HR-MS: [M]$^+$=537.2127 (calc. for C$_{23}$H$_{27}$N$_{11}$O$_5$: 537.2197); elemental analysis (calculated %-values for C$_{23}$H$_{27}$N$_{11}$O$_5$(HCl)$_5$ in parenthesis) C, 39.16 (38.38); H, 4.09 (4.48); N, 21.43 (21.40); O, (11.11); Cl, (24.63).

(c) Synthesis of $^{19}$F-Click Folate Standard

γ-(4-Azidobutyl)-folic acid amide (penta-hydrochloride salt, 14 mg, 0.02 mmol) was suspended in $^t$BuOH/H$_2$O (1:1, 2 mL) and 6-[$^{19}$F]fluoro-1-hexyne (48 mg, 0.2 mmol), Cu(OAc)$_2$ (0.8 mg, 20 mol %) and sodium ascorbate (1.5 mg, 40 mol %) were added. The mixture was stirred at 75° C. for 30 min after which HPLC indicated completed conversion of the azide starting material. The mixture was cooled to room temperature and the resulting suspension was dissolved by addition of a few drops NaOH 1M. Addition of HCl (1 M) to a final pH of 2 resulted in precipitation of the product. The mixture was centrifuged (10 min at 3500 rpm) and the pale yellow supernatant decanted. Drying of solid provided a brown powder (20 mg). The crude product was dissolved in NaOH 0.1 M (0.4 mL) and purified by semi-prep HPLC. The collected fractions containing the product were concentrated under reduced pressure and the residue dissolved in NaOH (1 M, 1 mL). Addition of HCl (1 M) to a final pH of 2 resulted in precipitation of the product. Centrifugation (10 min at 3500 rpm), decantation of the pale yellow supernatant and drying of the solid provided the penta-hydrochloride salt of the final product as a yellow powder (9 mg, 53%): $^1$H-NMR (DMSO-d6) δ 12.02-11.85 (bs, 1H), 8.66 (s, 1H), 8.19 (d, 1H, J=7.8 Hz), 7.86-7.80 (m, 2H), 7.65 (d, 2H, J=8.7 Hz), 7.35-6.95 (broad m, 2H), 6.65 (d, 2H, J=8.7 Hz), 4.53-4.47 (m, 3H), 4.40 (t, 1H, J=5.8 Hz), 4.32-4.23 (m, 3H), 3.54-3.32 (bs, 1H), 3.08-2.97 (m, 2H), 2.62 (t, 2H, J=6.6 Hz), 2.22-2.13 (m, 2H), 2.09-2.00 (m, 1H), 1.98-1.88 (m, 1H), 1.79-1.60 (m, 6H), 1.36-1.26 (m, 2H) ppm; $^{13}$C-NMR (DMSO-d6) δ 173.8, 171.5, 166.3, 160.7, 155.0, 153.5, 150.7, 149.1, 148.5, 146.5, 129.0, 128.0, 121.7, 121.4, 111.2, 84.2, 83.0, 52.2, 48.8, 45.9, 37.7, 32.0, 29.3, 27.2, 26.5, 26.1, 24.8, 24.5 ppm; LR-MS: [M+H]$^+$=638.24 (calc. for C$_{29}$H$_{36}$FN$_{11}$O$_5$: 637.67); elemental analysis (calculated %-values for C$_{29}$H$_{36}$N$_{11}$O$_5$(HCl)$_5$ in parenthesis) C, 42.72 (42.48); H, 5.18 (5.04); N, 18.17 (18.79); O, (9.76); F, (2.32); Cl, (21.62).

Example 2

Synthesis of $^{18}$F-Click Folate

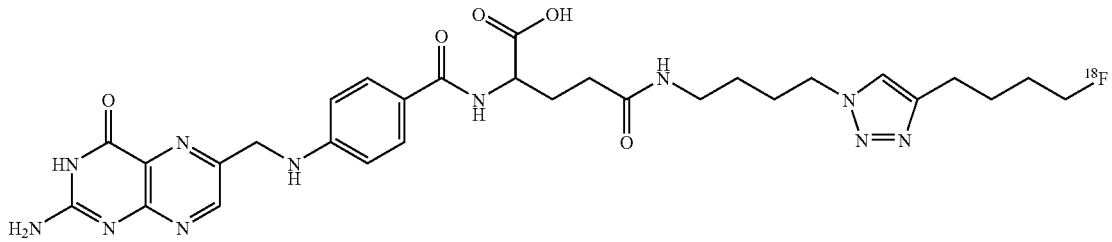

To the obtained dry [$^{18}$F]fluoride-cryptate complex 5-hexyn-1-yl p-tosylate (25 μl) in 1.2 ml acetonitrile was added. The reaction vessel was connected via a PTFE tubing with a second reaction vessel containing Copper(I) iodide (2.5 mg) and it was placed in a dry-ice/iso-propanol cooling bath. The reaction mixture in reaction vessel one was heated to 95-100° C. while the $^{18}$F-labelled product 6-[$^{18}$F]fluoro-1-hexyne was co-distilled with acetonitrile to the second reaction vessel (bp (6-[$^{18}$F]fluoro-1-hexyne)=106° C.). 6-[$^{18}$F]difluoro-1-hexyne was given in a radiochemical yield of 70-85% and a radiochemical purity of 90-98%. After 12 min the second reaction vessel containing 6-[$^{18}$F]fluoro-1-hexyne in ca. 0.8-1.0 ml acetonitrile was disconnected and allowed to warm to room temperature. To this mixture 0.3 ml water, 25 μl DIEA, 25 mg sodium ascorbate in 0.15 ml water and γ-(4-azido-butionyl)-folic acid amide (see Example 1(b)) in 0.2 ml DMF are added successively. The mixture was heated to 80° C. and was allowed to cool down to 60° C. within 20 min. The $^{18}$F-Click-folate content of the crude mixture was 55-65%.

For semi-preparative HPLC purification the mixture was diluted with 2 ml HPLC solvent. The separation was carried out on a RP 18 column (Phenomenex© Gemini 5μ C18, 250×10 mm) using a gradient as follows. Solvent A=10 mM ammonium bicarbonate solution, B=methanol, 0-30 min: A: 90%→40%, 30-40 min: A: 40% 40-45 min: A: 40%→90%.

The HPLC solvent of the isolated $^{18}$F-click folate was removed under reduced pressure and a stream of nitrogen at 100° C. The product was formulated in physiological phosphate buffer solution.

Example 3

In Vitro, In Vivo and Ex Vivo Studies Using $^{18}$F-Click Folate

The $^{18}$F-click folate was employed in in vitro plasma stability studies and in metabolite studies using liver microsomes.

$^{18}$F-click folate was incubated with both human and murine plasma at 37° C. in a shaking water bath. Aliquots were taken at different time points and analysed by HPLC. The tracer showed a high stability. No defluorination or other radioactive degradation products were detected over a period of 0-120 min.

Metabolites studies using human and murine liver microsomes were carried out at 37° C. over a time span of 0-30 min. Aliquots were taken at 0, 5, 15 and 30 min. The studies showed no radioactive metabolites or degradation of the $^{18}$F-click folate over 30 min.

$^{18}$F-click folate was applied in ex vivo biodistribution studies using eight nude mice bearing KB xenografts tumors. ~2 MBq of the radiotracer were injected into each animal. In a blockade group (4 animals) 200 lag natural folic acid was injected 10 min prior to the radiotracer. The animals were scarified 45 min post injection. The folate receptor-positive KB tumors show a high specific uptake of the radiotracer with a ratio of 94% specific blockade. Furthermore a specific uptake with 78% specific blockade was also found in the kidneys, which are known to express the folate receptor. High unspecific uptake was found in gallbladder, intestine and feces which points to a strong hepatobiliary elimination of the radiotracer.

Figure 3:
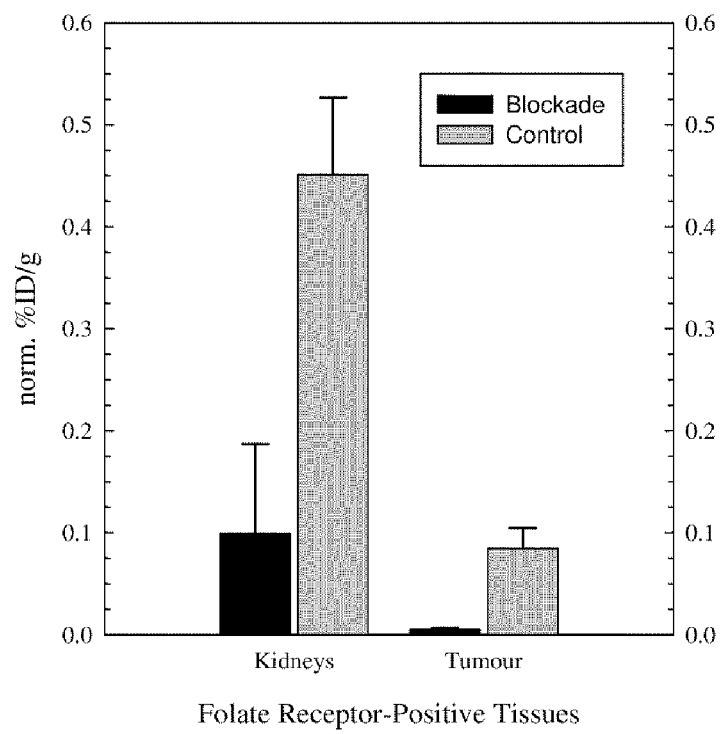
FIG. 3. Specific uptake in folate receptor-positive tissues as shown by ex vivo biodistribution studies using $^{18}$F-click folate.

FIG. 3 shows the high specific uptake of the $^{18}$F-click folate in folate receptor-positive tissues.

In vivo PET imaging using the $^{18}$F-click folate was performed in nude mice bearing KB xenografts tumors. ~11 MBq of the radiotracer were injected into each animal. In the blockade group 200 μg natural folic acid was injected 10 min prior to the radiotracer. The PET scans were acquired from 15 min to 45 min post injection.

The KB tumors could be imaged by PET using $^{18}$F-click folate. Due to a low tumor-to-background ratio, the KB tumors are only moderately visualized. A high accumulation of radioactivity in the abdominal region (gallbladder, intestines) points to a strong hepatobiliary elimination of the radiotracer.

PET imaging using [$^{18}$F]FDG was performed with the same animals four days after the $^{18}$F-click folate studies. ~9 MBq of [$^{18}$F]FDG were injected into each animal. The PET scans were acquired from 30 min to 60 min post injection. The [$^{18}$F]FDG scans were not able to image the folate receptor-positive KB tumors. Although [$^{18}$F]FDG is the most commonly used radiotracer in PET tumor imaging, it is known that [$^{18}$F]FDG is not suitable for the imaging of KB xenografts tumors (Bettio et al, J. Nucl. Med. 1998; 47: 1153-60).

Figure 4:
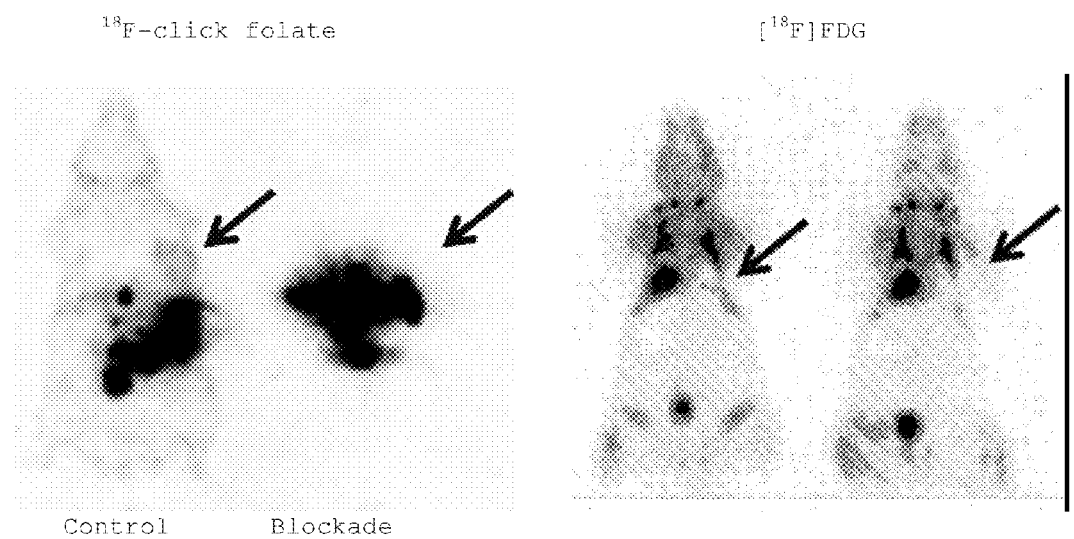
FIG. 4. PET images using $^{18}$F-click folate in comparison to PET images using [$^{18}$F]FDG.

FIG. 4 show the PET images using $^{18}$F-click folate (left hand side) in comparison to PET images using [$^{18}$F]FDG (right hand side), the arrows indicate the position of the KB xenografts tumors.

The invention claimed is:
1. A compound having formula II

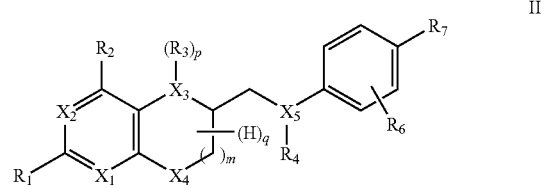

wherein
$X_1$ to $X_4$ are N,
$X_5$ is C or N,
$R_1$ is H, Hal, —OR', —NHR', C1-C12 alkyl, C1-C12 alkoxy, C1-C12 alkanoyl, C2-C12 alkenyl, C2-C12 alkynyl, (C1-C12 alkoxy)carbonyl, or (C1-C12 alkylamino)carbonyl, wherein R' is H or C1-C6 alkyl R2 is O, $R_3$, $R_4$ are independently of each other H, formyl, iminomethyl, nitroso, C1-C12 alkyl, C1-C12 alkoxy, C1-C12 alkanoyl, or halosubstituted C1-C12 alkanoyl, $R_5$ is H, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, or ($C_1$-$C_{12}$ alkylamino)carbonyl, $R_6$, $R_7$ are independently of each other straight-chain or branched $C_1$-$C_{12}$ alkyl, which is unsubstituted or substituted by at least one CN, Hal, or $NO_2$, or a group of the formula III

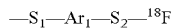   III wherein $S_1$ and $S_2$ are independently of each other a single bond, a spacer unit, a straight-chain or branched C1-C12 alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —$SO_3$R'—, —PR'—, or a five- or six-membered aromatic ring, which is unsubstituted or substituted with CN, Hal, $NO_2$, COR', or COOR', wherein R' represents H or $C_1$-$C_6$ alkyl, or a combination thereof, and $Ar_1$ is a triazole or a tetrazole, with the proviso that one of $R_6$ and $R_7$ is a group of formula III, m is 0 or 1, P is 0, 1 or 2, and q has a value of 1 to 7.

2. A compound according to claim 1, wherein $R_6$ is straight-chain or branched $C_1$-$C_{12}$ alkyl, which is unsubstituted or substituted by at least one CN, Hal, or $NO_2$, and $R_7$ is a group of formula III.

3. A compound according to claim 1, wherein $R_7$ is straight-chain or branched $C_1$-$C_{12}$ alkyl, which is unsubstituted or substituted by at least one CN, Hal, or $NO_2$, and $R_6$ is a group of formula III.

4. A compound according to claim 1 wherein $S_1$ is a single bond, a spacer unit, a straight-chain or branched $C_1$-$C_{18}$ alkyl, which is unsubstituted or substituted by at least one CN, Hal, or $NO_2$, and wherein one or more of non-adjacent $CH_2$ groups may independently be replaced by —O—, —CO—, —CO—O—, —NR'—, —NR'—CO—, —CO—NR'—, —CH=CH—, —C≡C—, or a five- or six-membered aromatic ring, which is unsubstituted or substituted with CN, Hal, $NO_2$, COR', or COOR', wherein R' represents H or $C_1$-$C_6$ alkyl, or a combination thereof.

5. A compound according to claim 1 wherein $S_2$ is a single bond or a straight-chain or branched $C_1$-$C_{12}$ alkyl, which is unsubstituted or substituted by at least one CN, Hal, or $NO_2$, or a five- or six-membered aromatic ring, which is unsubstituted or substituted with CN, Hal, $NO_2$, COR', or COOR', wherein R' represents H or $C_1$-$C_6$ alkyl, or a combination thereof.

6. A compound according to claim 1, which is of formula IV

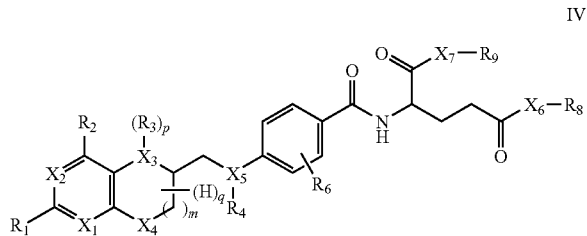   IV wherein $X_6$, $X_7$ are independently of each other C, N or O, $R_8$, $R_9$ are independently of each other H or straight-chain or branched $C_1$-$C_{12}$ alkyl, which is unsubstituted or substituted by at least one CN, Hal, or $NO_2$, and wherein one or more of embedded, non-adjacent CH2 groups may independently be replaced by —O—, —CO—, —CO—O—, —CO—NR'—, —CH=CH—, or —C≡C—, or a group of the formula V

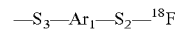   V wherein $S_2$, $S_3$ are independently of each other a single bond, a spacer unit, a straight chain or branched $C_1$-$C_{12}$ alkyl, which is unsubstituted or substituted by at least one CN, Hal, or $NO_2$, and wherein one or more of the non-adjacent CH2 groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —$SO_3$R'—, —PR'—, or a five- or six-membered aromatic ring, which is unsubstituted or substituted with CN, Hal, $NO_2$, COR', or COOR', wherein R'represents H or $C_1$-$C_6$ alkyl, or a combination thereof, $Ar_1$ is a triazole or a tetrazole, $X_1$ to $X_4$ are N, $X_5$ is C or N, $R_1$ is H, Hal, —OR', —NHR', C1-C12 alkyl, C1-C12 alkoxy, C1-C12 alkanoyl, C2-C12 alkenyl, C2-C12 alkynyl, (C1-C12 alkoxy)carbonyl, or (C1-C12 alkylamino)carbonyl, wherein R' is H or C1-C6 alkyl R2 is O, $R_3$, $R_4$ are independently of each other H, formyl, iminomethyl, nitroso, C1-C12 alkyl, C1-C12 alkoxy, C1-C12 alkanoyl, or halosubstituted C1-C12 alkanoyl, $R_5$ is H, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, (C1-C12 alkoxy)carbonyl, or ($C_1$-$C_{12}$ alkylamino)carbonyl, $R_6$ is a straight-chain or branched $C_1$-$C_{12}$ alkyl, which is unsubstituted or substituted by at least one CN, Hal, or $NO_2$, or a group of the formula III

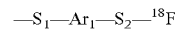   III wherein $S_1$ and $S_2$ are independently of each other a single bond, a spacer unit, a straight-chain or branched C1-C12 alkyl, which is unsubstituted or substituted by at least one CN, Hal, or $NO_2$, and wherein one or more of the non-adjacent $CH_2$ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —$SO_3$R'—, —PR'—, or a five- or six-membered aromatic ring, which is unsubstituted or substituted with CN, Hal, NO$_2$, COR', or COOR', wherein R' represents H or C$_1$-C$_6$ alkyl, or a combination thereof, and
Ar$_1$ is a triazole or a tetrazole,
m is 0 or 1,
p is 0, 1 or 2, and
q has a value of 1 to 7,
with the proviso that either R$_6$ is a group of formula III or at least one of R$_8$ and R$_9$ is a group of formula V.

7. A compound according to claim 6, wherein S$_2$ and S$_3$ are independently of each other a single bond or a straight chain or branched C$_1$-C$_{12}$ alkyl, which is unsubstituted or substituted by at least one CN, Hal, or NO$_2$, or a five- or six-membered aromatic ring, which is unsubstituted or substituted with CN, Hal, NO$_2$, COR', or COOR', wherein R' represents H or C$_1$-C$_6$ alkyl, or a combination thereof.

8. A compound according to claim 1 wherein Ar$_1$ is selected from formulae V-c, V-d and V-e

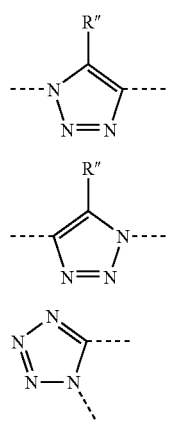

V-c
V-d
V-e wherein the dotted lines represent linking sites to the spacer groups and R" is H, Hal, NH—COR', NH—SO$_2$R', CO$_2$R', or COR', wherein R' represents H or C1-C6 alkyl, or straight-chain or branched C$_1$-C$_{12}$ alkyl, which is unsubstituted or substituted by at least one CN, Hal, OH, NH$_2$, SO$_3$H, SH, CO$_2$H, or NO$_2$, or a five- or six-membered aromatic ring, which is unsubstituted or substituted with CN, Hal, NO$_2$, COR', or COOR', wherein R' represents H or C$_1$-C$_6$ alkyl, or a combination thereof.

9. A compound according to claim 6, wherein R$_6$ is CN, Hal, NO$_2$, or a group R$_5$ and at least one of R$_8$ and R$_9$ is a group of formula V.

10. A compound according to claim 6, wherein R$_6$ is CN, Hal, NO$_2$, or a group R$_5$, R$_8$ is H or straight chain or branched C$_1$-C$_{12}$ alkyl, which is unsubstituted or substituted by at least one CN, Hal or NO$_2$, wherein one or more of embedded, non-adjacent CH2 groups may independently be replaced by —O—, —CO—, —CO—O—, —CO—NR'—, —CH=CH—, or —C≡C—, and R$_9$ is a group of formula V.

11. A compound according to claim 6, wherein R$_6$ is CN, Hal, NO$_2$, or a group R$_5$, R$_9$ is H or straight chain or branched C$_1$-C$_{12}$ alkyl, which is unsubstituted or substituted by at least one CN, Hal or NO$_2$, wherein one or more of embedded, non-adjacent CH2 groups may independently be replaced by —O—, —CO—, —CO—O—, —CO—NR'—, —CH=CH—, or —C≡C—, and R$_8$ is a group of formula V.

12. A compound according to claim 6, wherein R$_8$ and R$_9$ are independently of each other H or straight chain or branched C$_1$-C$_{12}$ alkyl, which is unsubstituted or substituted by at least one CN, Hal or NO$_2$, wherein one or more of embedded, non-adjacent CH2 groups may independently be replaced by —O—, —CO—, —CO—O—, —CO—NR'—, —CH=CH—, or —C≡C—, and R$_6$ is a group of formula V.

13. A compound according to claim 1 having one of formulae VI, VIa or VIb,

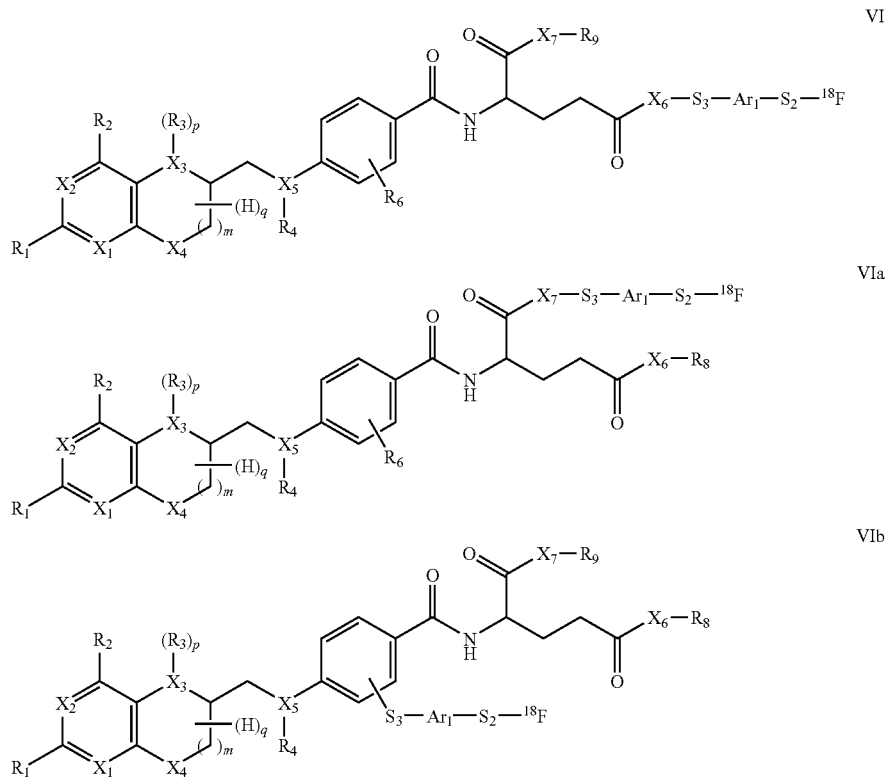

wherein
X₁ to X₄ are N,
X₅ is C or N,
X₆, X₇ are independently of each other C, N or O,
R₁ is H, Hal, —OR', —NHR', C1-C12 alkyl, C1-C12 alkoxy, C1-C12 alkanoyl, C2-C12 alkenyl, C2-C12 alkynyl, (C1-C12 alkoxy)carbonyl, or (C1-C12 alkylamino)carbonyl, wherein R' is H or C1-C6 alkyl R2 is O,
R₃, R₄ are independently of each other H, formyl, iminomethyl, nitroso, C1-C12 alkyl, C1-C12 alkoxy, C1-C12 alkanoyl, or halosubstituted C1-C12 alkanoyl,
R₆ is H, CN, Hal, NO₂, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, or ($C_1$-$C_{12}$ alkylamino)carbonyl,
R₈, R₉ are independently of each other H or straight chain or branched C1-C12 alkyl, which is unsubstituted or substituted by at least one CN, Hal, or NO2 and wherein one or more of embedded, non-adjacent CH2 groups may independently be replaced by —O—, —CO—, —CO—O—, —CO—NR'—, —CH=CH—, or —C≡C—,
S₂, S₃ are independently of each other a single bond, a spacer unit, a straight-chain or branched $C_1$-$C_{12}$ alkyl, which is unsubstituted or substituted by at least one CN, Hal, or NO₂, and wherein one or more of the non-adjacent CH₂ groups may independently be replaced by —O—, —CO—, —CO—O—, —O—CO—, —NR'—, —N=, —NR'—CO—, —CO—NR'—, —NR'—CO—O—, —O—CO—NR'—, —NR'—CO—NR'—, —CH=CH—, —C≡C—, —S—, —SO₃R'—, —PR'—, or a five- or six-membered aromatic ring, which is unsubstituted or substituted with CN, Hal, NO₂, COR', or COOR', wherein R' represents H or $C_1$-$C_6$ alkyl, or a combination thereof,
Ar₁ is a triazole or a tetrazole,
m is 0 or 1,
P is 0, 1 or 2, and
q has a value of 1 to 7.

14. A compound according to claim 13 wherein S₂ and S₃ are independently of each other a single bond or a straight-chain or branched $C_1$-$C_{12}$ alkyl, which is unsubstituted or substituted by at least one CN, Hal, or NO₂, or a five- or six-membered aromatic ring, which is unsubstituted or substituted with CN, Hal, NO₂, COR', or COOR', wherein R' represents H or $C_1$-$C_6$ alkyl.

15. A compound according to claim 13, wherein Ar₁ is selected from formulae V-c, V-d and V-e

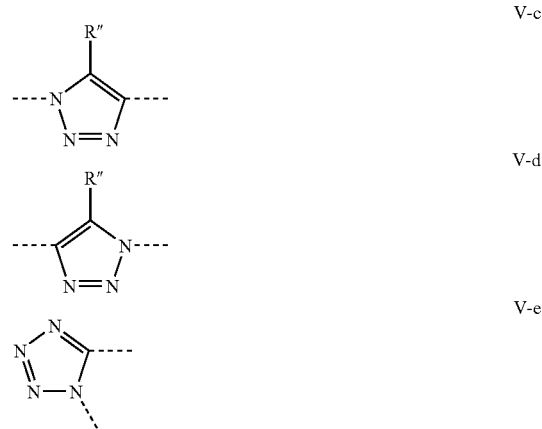

wherein the dotted lines represent linking sites to the spacer groups and R" is H, Hal, NH—COR', NH—SO₂R', CO₂R', or COR', wherein R' represents H or C1-C6 alkyl, or straight-chain or branched C1-C12 alkyl, which is unsubstituted or substituted by at least one CN, Hal, OH, NH₂, SO₃H, SH, CO₂H, or NO₂, or a five- or six-membered aromatic ring, which is unsubstituted or substituted with CN, Hal, NO₂, COR', or COOR', wherein R' represents H or $C_1$-$C_6$ alkyl, or a combination thereof.

16. A compound according to claim 1, which is one of formulae VIIa to VIIf or VIIIa to VIIIf,

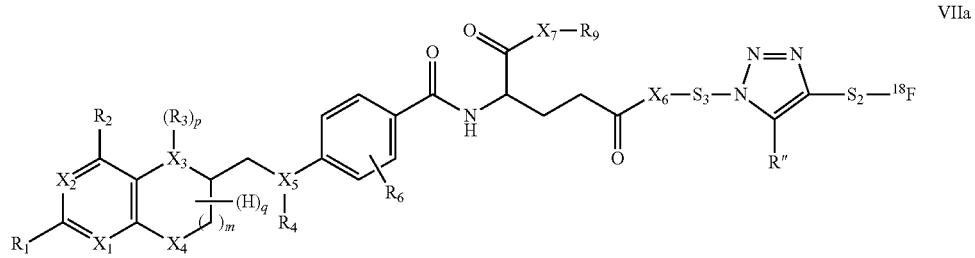

VIIa

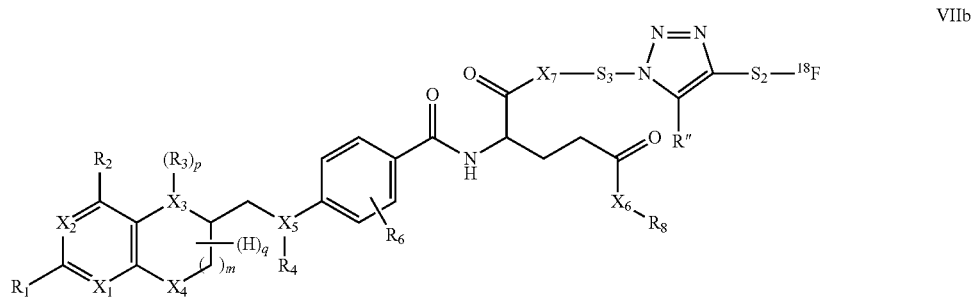

VIIb

-continued
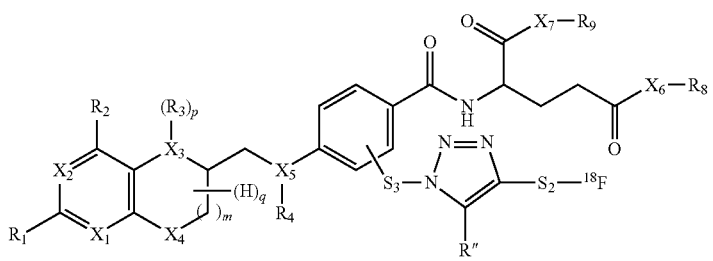
VIIc
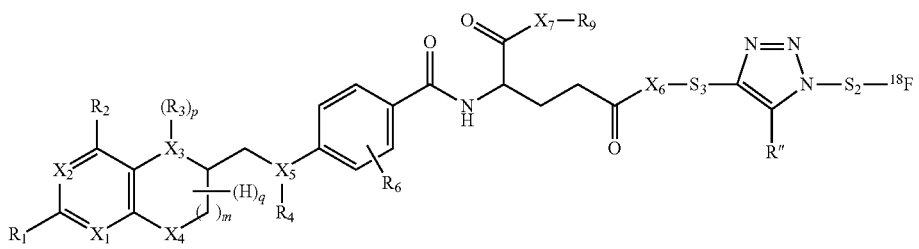
VIId
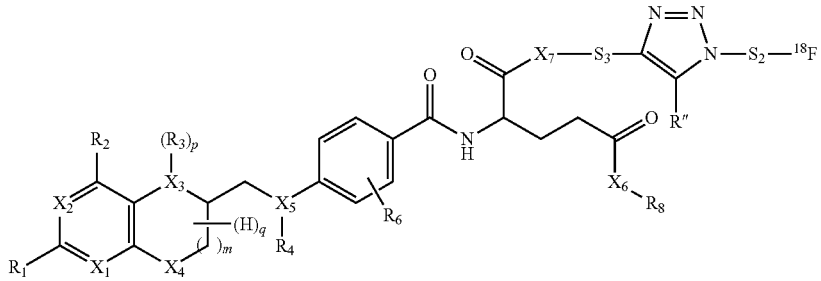
VIIe
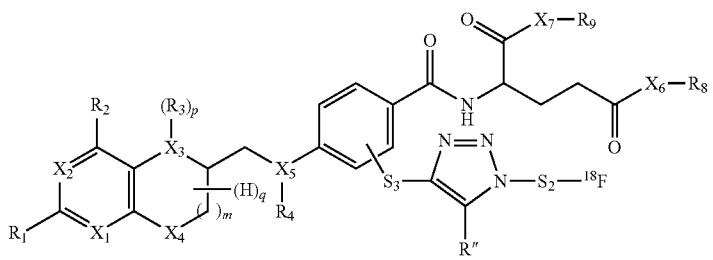
VIIf
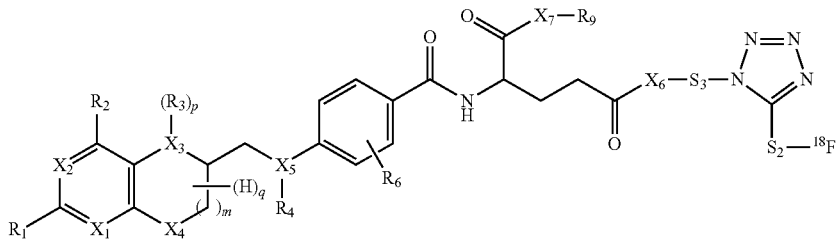
VIIIa
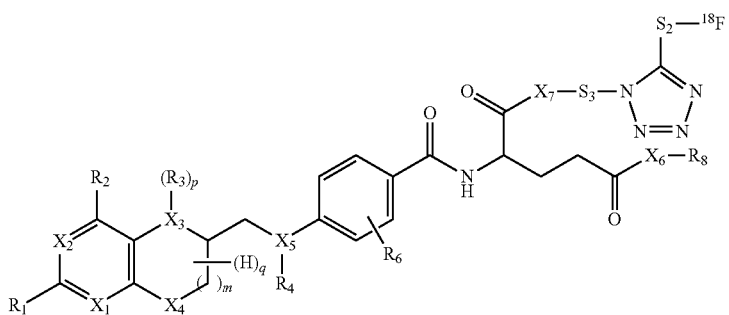
VIIIb -continued VIIIc VIIId VIIIe VIIIf wherein
$X_1$ to $X_4$ are N,
$X_5$ is C or N,
$X_6$, $X_7$ are independently of each other C, N or O,
$R_1$ is H, Hal, —OR', —NHR', C1-C12 alkyl, C1-C12 alkoxy, C1-C12 alkanoyl, C2-C12 alkenyl, C2-C12 alkynyl, (C1-C12 alkoxy)carbonyl, or (C1-C12 alkylamino)carbonyl, wherein R' is H or C1-C6 alkyl R2 is O,
$R_3$, $R_4$ are independently of each other H, formyl, iminomethyl, nitroso, C1-C12 alkyl, C1-C12 alkoxy, C1-C12 alkanoyl, or halosubstituted C1-C12 alkanoyl,
$R_6$ is H, CN, Hal, $NO_2$, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, or ($C_1$-$C_{12}$ alkylamino)carbonyl,
$R_8$, $R_9$ are independently of each other H or straight chain or branched C1-C12 alkyl, which is unsubstituted or substituted by at least one CN, Hal, or NO2 and wherein one or more of embedded, non-adjacent CH2 groups may independently be replaced by —O—, —CO—, —CO—O—, —CO—NR'—, —CH=CH—, or —C≡C—, $S_2$, $S_3$ are independently of each other a single bond, a spacer unit, a straight-chain or branched $C_1$-$C_{12}$ alkyl, which is unsubstituted or substituted by at least one CN, Hal, or $NO_2$, and wherein one or more of the non-adjacent CH2 groups may independently be replaced by —O—, —CO—, —CO—O—, —O—CO—, —NR'—, —N=, —NR'—CO—, —CO—NR', —NR'—CO—O—, —O—CO—NR'—, —NR'—CO—NR'—, —CH=CH—, —C≡C—, —S—, —$SO_3R'$—, —PR'—, or a five- or six-membered aromatic ring, which is unsubstituted or substituted with CN, Hal, $NO_2$, COR', or COOR', wherein R' represents H or $C_1$-$C_6$ alkyl, or a combination thereof,
R" is H, Hal, NH—COR', NH—$SO_2R'$, $CO_2R'$, COR', or straight-chain or branched $C_1$-$C_{12}$ alkyl, which is unsubstituted or substituted by at least one CN, Hal, OH, $NH_2$, $SO_3H$, SH, $CO_2H$, or $NO_2$, or a five- or six-membered aromatic ring, which is unsubstituted or substituted with CN, Hal, $NO_2$, COR', or COOR', wherein R' represents H or $C_1$-$C_6$ alkyl, m is 0 or 1, P is 0, 1 or 2, and q has a value of 1 to 7.

17. A compound according to claim 16, wherein $R_1$ is H, alkyl, —OR', or —NHR', wherein R' represents H or $C_1$-$C_6$ alkyl.

18. A compound according to claim 16, wherein $R_3$ is H, formyl, C1-C12 alkyl or C1-C12 alkanoyl.

19. A compound according to claim 16, wherein $R_4$ is H, nitroso, C1-C12 alkoxy, or C1-C12 alkanoyl.

20. A compound according to claim 16, wherein $R_5$ is H, C1-C12 alkyl, C1-C12 alkoxy, C1-C12 alkanoyl, ($C_1$-$C_{12}$ alkoxy)carbonyl, or ($C_1$-$C_{12}$ alkylamino)carbonyl.

21. A compound according to claim 16, wherein $R_6$ is H, CN, Hal, $NO_2$, $C_1$-$C_{12}$ alkyl, $C_1$-$C_{12}$ alkoxy, $C_1$-$C_{12}$ alkanoyl, or ($C_1$-$C_{12}$ alkoxy)carbonyl.

22. A compound according to claim 1, having one of formulae IX, IXa, X or Xa, wherein, $X_6$, $X_7$ are independently of each other C, N or O, $Y_1$, $Y_2$ are independently of each other H, formyl, or straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, or —C≡C—, $Y_3$ is H, formyl, nitroso, or straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, or —C≡C—, $R_8$, $R_9$ are independently of each other H or straight chain or branched C1-C12 alkyl, which is unsubstituted or substituted by at least one CN, Hal, or NO2, and wherein one or more of embedded, non-adjacent CH2 groups

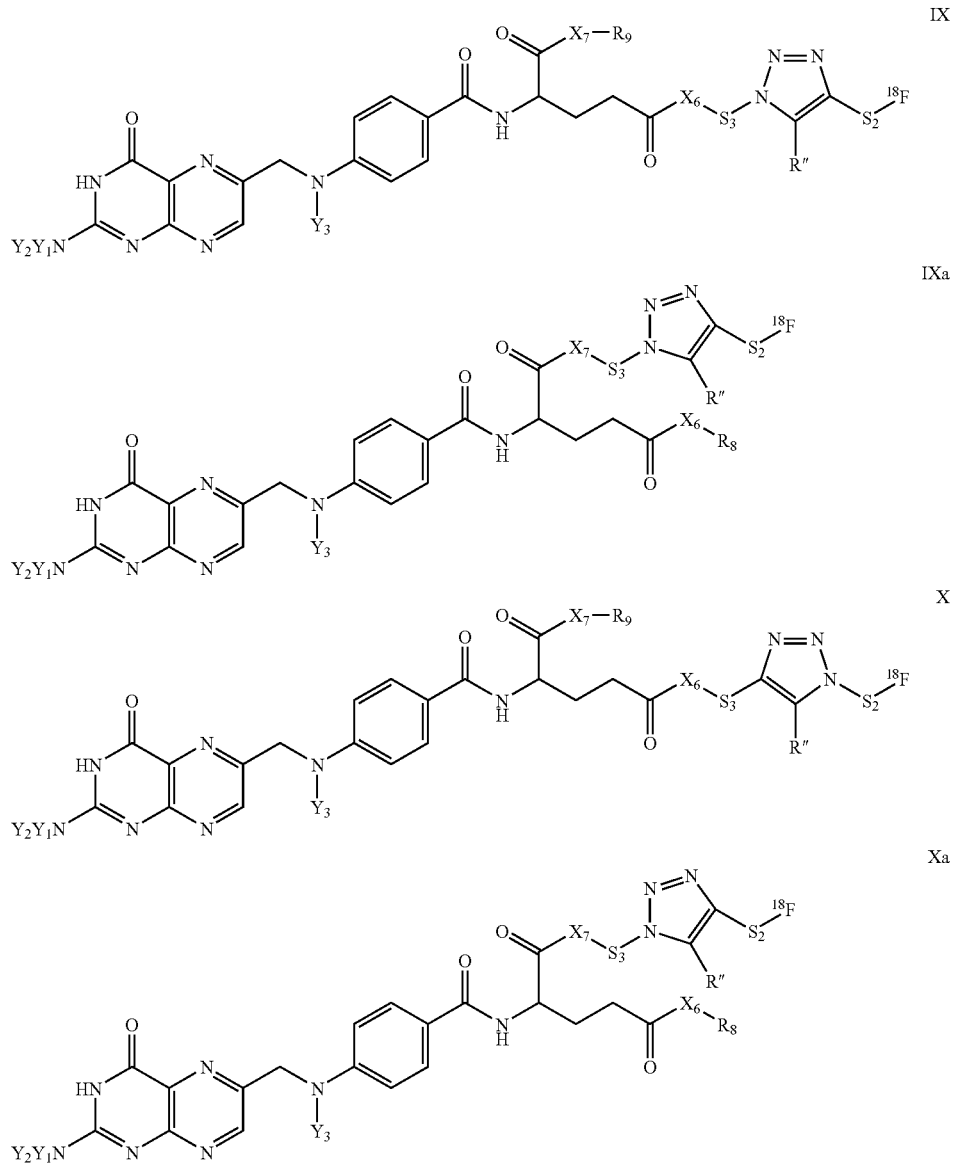

may independently be replaced by —O—, —CO—, —CO—O—, —CO—NR'—, —CH═CH—, or —C≡C—, R'' is H, Hal, NH—COR', NH—SO$_2$R', CO$_2$R', or COR', wherein R' represents H or C1-C6 alkyl, or straight-chain or branched C1-C12 alkyl, which is unsubstituted or substituted by at least one CN, Hal, OH, NH$_2$, SO$_3$H, SH, CO$_2$H, or NO$_2$, or a five- or six-membered aromatic ring, which is unsubstituted or substituted with CN, Hal, NO$_2$, COR', or COOR', wherein R' represents H or C$_1$-C$_6$ alkyl, or a combination thereof, and S$_2$, S$_3$ are independently of each other a single bond, a spacer unit, a straight-chain or branched C1-C12 alkyl, which is unsubstituted or substituted by at least one CN, Hal, or NO$_2$, and wherein one or more of the non-adjacent CH2 groups may independently be replaced by —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, or a five- or six-membered aromatic ring, which is unsubstituted or substituted with CN, Hal, NO$_2$, COR', or COOR', wherein R' represents H or C1-C6 alkyl, or a combination thereof.

23. A compound according to claim 22, wherein S$_2$ and S$_3$ are independently of each other straight-chain or branched C1-C8 alkyl, which is unsubstituted or substituted by at least one CN, Hal, or NO$_2$, or a five- or six-membered aromatic ring, which is unsubstituted or substituted with CN, Hal, NO$_2$, COR', or COOR', wherein R' represents H or C1-C6 alkyl.

* * * * *

UNITED STATES PATENT AND TRADEMARK OFFICE
CERTIFICATE OF CORRECTION

| | | |
|---|---|---|
| PATENT NO. | : 8,344,140 B2 | Page 1 of 1 |
| APPLICATION NO. | : 12/595297 | |
| DATED | : January 1, 2013 | |
| INVENTOR(S) | : Simon Mensah Ametamey et al. | |

It is certified that error appears in the above-identified patent and that said Letters Patent is hereby corrected as shown below:

Column 30, Line 45 reads: "lamino)carbonyl, wherein R' is H or Cl-C6 alkyl R2 is" should read
-- lamino)carbonyl, wherein R' is H or Cl-C6 alkyl
$R_2$ is O, --.

Column 30, Line 46, delete: "O,".

Column 33, Line 8 reads: "lamino)carbonyl, wherein R' is H or Cl-C6 alkyl R2is O," should read
-- lamino)carbonyl, wherein R' is H or Cl-C6 alkyl
$R_2$ is O, --.

Column 34, Line 33 reads: "NH-$50_2$R', $CO_2$R', or COR', wherein R' represents H or" should read -- NH-$SO_2$R', $CO_2$R', or COR', wherein R' represents H or --.

Column 37, Line 54 reads: "lamino)carbonyl, wherein R' is H or C1-C6 alkyl R2 is" should read -- lamino)carbonyl, wherein R' is H or C1-C6 alkyl
$R_2$ is O, --.

Column 37, Line 55, delete: "O,".

Column 38, Line 67 reads: "R'represents H or $C_1$-$C_6$ alkyl," should read -- R' represents H or $C_1$-$C_6$ alkyl, --.

Signed and Sealed this
Second Day of April, 2013

Teresa Stanek Rea
*Acting Director of the United States Patent and Trademark Office*